United States Patent [19]
Petka et al.

[11] Patent Number: 6,090,911
[45] Date of Patent: Jul. 18, 2000

[54] REVERSIBLE HYDROGELS

[75] Inventors: Wendy A. Petka, St. Paul, Minn.;
David A. Tirrell, Sunderland, Mass.;
Kevin P. McGrath, Alpharetta, Ga.

[73] Assignee: University of Massachusetts, Boston, Mass.

[21] Appl. No.: 08/956,307

[22] Filed: Oct. 22, 1997

[51] Int. Cl.[7] .......................... C07K 14/00; A61K 31/74; A61K 38/00
[52] U.S. Cl. .......................... 530/300; 530/350; 424/445; 424/78.02; 424/78.06; 514/2
[58] Field of Search .................... 530/300, 350; 424/445, 78.02, 78.06; 514/2

[56] References Cited

U.S. PATENT DOCUMENTS 5,243,038   9/1993   Ferrari et al. ........................... 536/23.1

OTHER PUBLICATIONS

Morii, H. et al., Bull. Chem. Soc. Jpn., vol. 64, No. 2, pp. 396–402, 1991.

McGrath et al., "Genetically Directed Syntheses of New Polymeric Materials. Expression of Artificial Genes Encoding Proteins with Repeating –(AlaGly)$_3$ProGluGly–Elements," *J. Am. Chem. Soc.*, 114(2):727–733, 1992.

McGrath and Kaplan, "Self–Assembling Nanostructures: Recognition and Ordered Assembly in Protein–Based Materials," *Mat. Res. Soc. Symp. Proc.*, 292:83–91, 1993.

McGrath and Kaplan, "Control of Molecular Organization in Protein–Based Materials," *Polym. Preprints*, 34(1):102–103, 1993.

Petka et al., "Surface Recognition and Diffusion of Engineered Macromolecules," Polymer Preprints, vol. 35(2), pp. 452–453, 1994.

*Primary Examiner*—Ponnathapu Achutamurthy
*Assistant Examiner*—Peter P. Tung
*Attorney, Agent, or Firm*—Fish & Richardson P.C.

[57] ABSTRACT

The invention is based on the discovery that a block copolymer that includes α-helical blocks, e.g., terminal blocks, which form intermolecular coiled-coil structures, and one or more random-coil blocks, which link the α-helical blocks, can form suspensions that can reversibly gel to form monodisperse hydrogels. The transition between the gel and liquid phases depends on pH, temperature, concentration, and chemical structure. The copolymers can be synthesized biologically through genetic engineering.

30 Claims, 29 Drawing Sheets

N' MRGSHHHHHHGSMA - Helix - IGDLNNTSGIRRPAAKLN C'
(SEQ ID NO:3)                    (SEQ ID NO:4)

Helix = SGDLENEVAQLEREVRSLEDEAAELEQKVSRLKNEIEDLKAE = A1 (SEQ ID NO:1)

Helix = SGDLKNKVAQLKRKVRSLKDKAAELKQEVSRLENEIEDLKAK = B1 (SEQ ID NO:2)

```
        EcoRI        BamHI                                              NheI
5'    AA   TTC    GGA  TCC   GAT  GAC  GAT  GAC  AAA   GCT  AGC
3'           G   CCT  AGG   CTA  CTG  CTA  CTG  TTT   CGA  TCG

NruI             BstEII              SphI              SpeI
      TAT  CGC  GAT   GGT  GAC  CCG   CGC  ATG  CCG   ACT  AGT
      ATA  GCG  CTA   CCA  CTG  GGC   GCG  TAC  GGC   TGA  TCA

BamHI        HindIII
      TGG  TAA    GGA  TCC    A                3'  (SEQ ID NO:5)
      ACC  ATT    CCT  AGG   TTC   GA          5'  (SEQ ID NO:6)
```

FIG. 6A (b)
```
        EcoRI        BamHI                                              NheI
5'    AA   TTC    GGA  TCC   GAT  GAC  GAT  GAC  AAA   TGG   GCT
3'           G   CCT  AGG   CTA  CTG  CTA  CTG  TTT   ACC   CGA

BstEII                       XhoI              SpeI
      AGC   GGT  GAC  CAT   GTG  GCG   CCT  CGA  GAC   ACT  AGT
      TCG   CCA  CTG  GTA   CAC  CGC   GGA  GCT  CTG   TGA  TCA

BamHI        HindIII
      ATG  GGT  GGC  TGC  TA    GGA  TCC    A           3'  (SEQ ID NO:7)
      TAC  CCA  CCG  ACG  AT    CCT  AGG   TTC   GA     5'  (SEQ ID NO:8)
```

FIG. 6B

```
       NruI              BanI
5'    C GAT CCG ATG GGT GCC GGC GCT GGT GCG GGC
3'    G CTA GGC TAC CCA CGG CCG CGA CCA CGC CCG

CCG GAA GGT GCA GGC GCT GGT GCG GGC CCG GAA
     GGC CTT CCA CGT CCG CGA CCA CGC CCG GGC CTT
     BanI
     GGT GCC GGC GCT GGT GCG GGC GGC GAA GGT GCA
     CCA CGG CCG CGA CCA CGC CCG CCG CTT CCA CGT
                                         BanI
     GGC GCT GGT GCG GGC CCG GAA GGT GCC GGC GCT
     CCG CGA CCA CGC CCG GGC CTT CCA CGG CCG CGA

GGT GCG GGC CCG GAA GGT GCA GGC GCT GGT GCG
     CCA CGC CCG GGC CTT CCA CGT CCG CGA CCA CGC
                 BanI
     GGC CCG GAA GGT GCC GGC GCT GGT GCG GGC CCG
     CCG GGC CTT CCA CGG CCG CGA CCA CGC CCG GGC
                                              BanI
     GAA GGT GCA GGC GCT GGT GCG GGC CCG GAA GGT
     CTT CCA CGT CCG CGA CCA CGC CCG GGC CTT CCA

GCC GGC GCT GGT GCG GGC CCG GAA GGT GCA GGC
     CGG CCG CGA CCA CGC CCG GGC CTT CCA CGT CCG
                                 BanI     SphI
     GCT GGT GCG GGC CCG GAA GGT GCC CGC ATG  3'
     CGA CCA CGC CCG GGC CTT CCA CGG GC       5'
     (SEQ ID NO:9)
     (SEQ ID NO:10)
```

FIG. 8

```
        NruI                    BanI
   5'  C GAT  CCG  ATG  GGT  GCC  GGC  GCT  GGT  GCG  GGC
   3'  G CTA  GGC  TAC  CCA  CGG  CCG  CGA  CCA  CGC  CCG

CCG  GAA  GGT  GCA  GGC  GCT  GGT  GCG  GGC  CCG  GAA
       GGC  CTT  CCA  CGT  CCG  CGA  CCA  CGC  CCG  GGC  CTT
       BanI
       GGT  GCC  GGC  GCT  GGT  GCG  GGC  GGC  GAA  GGT  GCA
       CCA  CGG  CCG  CGA  CCA  CGC  CCG  CCG  CTT  CCA  CGT
                                                 BanI
       GGC  GCT  GGT  GCG  GGC  CCG  GAA  GGT  GCC  GGC  GCT
       CCG  CGA  CCA  CGC  CCG  GGC  CTT  CCA  CGG  CCG  CGA

GGT  GCG  GGC  CCG  GAA  GGT  GCA  GGC  GCT  GGT  GCG
       CCA  CGC  CCG  GGC  CTT  CCA  CGT  CCG  CGA  CCA  CGC
                      BanI
       GGC  CCG  GAA  GGT  GCC  GGC  GCT  GGT  GCG  GGC  CCG
       CCG  GGC  CTT  CCA  CGG  CCG  CGA  CCA  CGC  CCG  GGC
                                                         BanI
       GAA  GGT  GCA  GGC  GCT  GGT  GCG  GGC  CCG  GAA  GGT
       CTT  CCA  CGT  CCG  CGA  CCA  CGC  CCG  GGC  CTT  CCA

GCC  GGC  GCT  GGT  GCG  GGC  CCG  GAA  GGT  GCA  GGC
       CGG  CCG  CGA  CCA  CGC  CCG  GGC  CTT  CCA  CGT  CCG
                                        BanI
       GCT  GGT  GCG  GGC  CCG  GAA  GGT  GCC  GGC  GCT  GGT
       CGA  CCA  CGC  CCG  GGC  CTT  CCA  CGG  CCG  CGA  CCA

GCG  GGC  CCG  GAA  GGT  GCA  GGC  GCT  GGT  GCG  GGC
       CGC  CCG  GGC  CTT  CCA  CGT  CCG  CGA  CCA  CGC  CCG
                 BanI
       CCG  GAA  GGT  GCC  GGC  GCT  GGT  GCG  GGC  CCG  GAA
       GGC  CTT  CCA  CGG  CCG  CGA  CCA  CGC  CCG  GGC  CTT
```

FIG. 9A

```
                                                              BanI
GGT  GCA  GGC  GCT  GGT  GCG  GGC  CCG  GAA  GGT  GCC
CCA  CGT  CCG  CGA  CCA  CGC  CCG  GGC  CTT  CCA  CGG

GGC  GCT  GGT  GCG  GGC  CCG  GAA  GGT  GCA  GGC  GCT
CCG  CGA  CCA  CGC  CCG  GGC  CTT  CCA  CGT  CCG  CGA
                         BanI
GGT  GCG  GGC  CCG  GAA  GGT  GCC  GGC  GCT  GGT  GCG
CCA  CGC  CCG  GGC  CTT  CCA  CGG  CCG  CGA  CCA  CGC

GGC  CCG  GAA  GGT  GCA  GGC  GCT  GGT  GCG  GGC  CCG
CCG  GGC  CTT  CCA  CGT  CCG  CGA  CCA  CGC  CCG  GGC
         BanI
GAA  GGT  GCC  GGC  GCT  GGT  GCG  GGC  CCG  GAA  GGT
CTT  CCA  CGG  CCG  CGA  CCA  CGC  CCG  GGC  CTT  CCA
                                             BanI
GCA  GGC  GCT  GGT  GCG  GGC  CCG  GAA  GGT  GCC  GGC
CGT  CCG  CGA  CCA  CGC  CCG  GGC  CTT  CCA  CGG  CCG

GCT  GGT  GCG  GGC  CCG  GAA  GGT  GCA  GGC  GCT  GGT
CGA  CCA  CGC  CCG  GGC  CTT  CCA  CGT  CCG  CGA  CCA
                         BanI
GCG  GGC  CCG  GAA  GGT  GCC  GGC  GCT  GGT  GCG  GGC
CGC  CCG  GGC  CTT  CCA  CGG  CCG  CGA  CCA  CGC  CCG

CCG  GAA  GGT  GCA  GGC  GCT  GGT  GCG  GGC  CCG  GAA
GGC  CTT  CCA  CGT  CCG  CGA  CCA  CGC  CCG  GGC  CTT
BanI
GGT  GCC  GGC  GCT  GGT  GCG  GGC  CCG  GAA  GGT  GCA
CCA  CGG  CCG  CGA  CCA  CGC  CCG  GGC  CTT  CCA  CGT
                                   BanI
GGC  GCT  GGT  GCG  GGC  CCG  GAA  GGT  GCC  GGC  GCT
CCG  CGA  CCA  CGC  CCG  GGC  CTT  CCA  CGG  CCG  CGA

GGT  GCG  GGC  CCG  GAA  GGT  GCA  GGC  GCT  GGT  GCG
CCA  CGC  CCG  GGC  CTT  CCA  CGT  CCG  CGA  CCA  CGC
                    BanI          SphI
GGC  CCG  GAA  GGT  GCC  CGC  ATG  3'  (SEQ ID NO:11)
CCG  GGC  CTT  CCA  CGG  GC        5'  (SEQ ID NO:12)
```

FIG. 9B

```
       BstEII
5'  GT  GAC  CTG  GAA  AAC  GAA  GTG  GCC  CAG  CTG  GGA
3'            GAC  CTT  TTG  CTT  CAC  CGG  GTC  GAC  CTT
                        BglII
    AGG  GAA  GTT  AGA  TCT  CTG  GAA  GAT  GAA  GCG  GCT
    TCC  CTT  CAA  TCT  AGA  GAC  CTT  CTA  CTT  CGC  CGA
                                  XhoI
    GAA  CTG  GAA  CAA  AAA  GTC  TCG  AGA  CTG  AAA  AAT
    CTT  GAC  CTT  GTT  TTT  CAG  AGC  TCT  GAC  TTT  TTA
                                                      BstEII
    GAA  ATC  GAA  GAC  CTG  AAA  GCC  GAA  ATT  G         5'
    CTT  TAG  CTT  CTG  GAC  TTT  CGG  CTT  TAA  CCA CTG 3'
    (SEQ ID NO:13)
    (SEQ ID NO:14)
```

FIG. 10A

```
       BstEII
5'  GT  GAC  CTG  AAA  AAC  AAA  GTG  GCC  CAG  CTG  AAA
3'            GAC  TTT  TTG  TTT  CAC  CGG  GTC  GAC  TTT
                        BglII
    AGG  AAA  GTT  AGA  TCT  CTG  AAA  GAT  AAA  GCG  GCT
    TCC  TTT  CAA  TCT  AGA  GAC  TTT  CTA  TTT  CGC  CGA
                                  XhoI
    GAA  CTG  AAA  CAA  GAA  GTC  TCG  AGA  CTG  GAA  AAT
    CTT  GAC  TTT  GTT  CTT  CAG  AGC  TCT  GAC  CTT  TTA
                                                      BstEII
    GAA  ATC  GAA  GAC  CTG  AAA  GCC  AAA  ATT  G         5'
    CTT  TAG  CTT  CTG  GAC  TTT  CGG  TTT  TAA  CCA CTG 3'
    (SEQ ID NO:15)
    (SEQ ID NO:16)
```

FIG. 10B

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 42 amino acids
       (B) TYPE: amino acid
       (D) TOPOLOGY: linear (ii) MOLECULE TYPE: peptide (xi) SEQUENCE DESCRIPTION: SEQ ID NO:1:

Ser Gly Asp Leu Glu Asn Glu Val Ala Gln Leu Glu Arg Glu Val Arg
 1               5                  10                  15

Ser Leu Glu Asp Glu Ala Ala Glu Leu Glu Gln Lys Val Ser Arg Leu
                20                  25                  30

Lys Asn Glu Ile Glu Asp Leu Lys Ala Glu
            35                  40

(2) INFORMATION FOR SEQ ID NO:2:

(i) SEQUENCE CHARACTERISTICS:
       (A) LENGTH: 42 amino acids
       (B) TYPE: amino acid
       (D) TOPOLOGY: linear (ii) MOLECULE TYPE: peptide (xi) SEQUENCE DESCRIPTION: SEQ ID NO:2:

Ser Gly Asp Leu Lys Asn Lys Val Ala Gln Leu Lys Arg Lys Val Arg
 1               5                  10                  15

Ser Leu Lys Asp Lys Ala Ala Glu Leu Lys Gln Glu Val Ser Arg Leu
                20                  25                  30

Glu Asn Glu Ile Glu Asp Leu Lys Ala Lys
            35                  40

(2) INFORMATION FOR SEQ ID NO:3:

(i) SEQUENCE CHARACTERISTICS:
       (A) LENGTH: 14 amino acids
       (B) TYPE: amino acid
       (D) TOPOLOGY: linear (ii) MOLECULE TYPE: peptide (xi) SEQUENCE DESCRIPTION: SEQ ID NO:3:

Met Arg Gly Ser His His His His His His Gly Ser Met Ala
 1               5                  10

(2) INFORMATION FOR SEQ ID NO:4:

(i) SEQUENCE CHARACTERISTICS:
       (A) LENGTH: 18 amino acids
       (B) TYPE: amino acid
       (D) TOPOLOGY: linear (ii) MOLECULE TYPE: peptide (xi) SEQUENCE DESCRIPTION: SEQ ID NO:4:

Ile Gly Asp Leu Asn Asn Thr Ser Gly Ile Arg Arg Pro Ala Ala Lys
 1               5                  10                  15

Leu Asn (2) INFORMATION FOR SEQ ID NO:5:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
AATCGGATCC GATGACGATG ACAAAGCTAG CTATCGCGAT GGTGACCCGC GCATGCCGAC      60

TAGTTGGTAA GGATCCA                                                    77
```

(2) INFORMATION FOR SEQ ID NO:6:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
AGCTTGGATC CTTACCAACT AGTCGGCATG CGCGGGTCAC CATCGCGATA GCTAGCTTTG      60

TCATCGTCAT CGGATCCG                                                   78
```

(2) INFORMATION FOR SEQ ID NO:7:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
AATTCGGATC CGATGACGAT GACAAATGGG CTAGCGGTGA CCATGTGGCG CCTCGAGACA      60

CTAGTATGGG TGGCTGCTAG GATCCA                                          86
```

(2) INFORMATION FOR SEQ ID NO:8:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
AGCTTGGATC CTAGCAGCCA CCCATACTAG TGTCTCGAGG CGCCACATGG TCACCGCTAG      60

CCCATTTGTC ATCGTCATCG GATCCG                                          86
```

(2) INFORMATION FOR SEQ ID NO:9:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

| | | | | | |
|---|---|---|---|---|---|
| CGATCCGATG | GGTGCCGGCG | CTGGTGCGGG | CCCGGAAGGT | GCAGGCGCTG | GTGCGGGCCC | 60 |
| GGAAGGTGCC | GGCGCTGGTG | CGGGCGGCGA | AGGTGCAGGC | GCTGGTGCGG | GCCCGGAAGG | 120 |
| TGCCGGCGCT | GGTGCGGGCC | CGGAAGGTGC | AGGCGCTGGT | GCGGGCCCGG | AAGGTGCCGG | 180 |
| CGCTGGTGCG | GGCCCGGAAG | GTGCAGGCGC | TGGTGCGGGC | CCGGAAGGTG | CCGGCGCTGG | 240 |
| TGCGGGCCCG | GAAGGTGCAG | GCGCTGGTGC | GGGCCCGGAA | GGTGCCCGCA | TG | 292 |

(2) INFORMATION FOR SEQ ID NO:10:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

| | | | | | |
|---|---|---|---|---|---|
| CGGGCACCTT | CCGGGCCCGC | ACCAGCGCCT | GCACCTTCCG | GGCCCGCACC | AGCGCCGGCA | 60 |
| CCTTCCGGGC | CCGCACCAGC | GCCTGCACCT | TCCGGGCCCG | CACCAGCGCC | GGCACCTTCC | 120 |
| GGGCCCGCAC | CAGCGCCTGC | ACCTTCCGGG | CCCGCACCAG | CGCCGGCACC | TTCCGGGCCC | 180 |
| GCACCAGCGC | CTGCACCTTC | GCCGCCCGCA | CCAGCGCCGG | CACCTTCCGG | GCCCGCACCA | 240 |
| GCGCCTGCAC | CTTCCGGGCC | CGCACCAGCG | CCGGCACCCA | TCGGATCG | | 288 |

(2) INFORMATION FOR SEQ ID NO:11:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

| | | | | | |
|---|---|---|---|---|---|
| CGATCCGATG | GGTGCCGGCG | CTGGTGCGGG | CCCGGAAGGT | GCAGGCGCTG | GTGCGGGCCC | 60 |
| GGAAGGTGCC | GGCGCTGGTG | CGGGCGGCGA | AGGTGCAGGC | GCTGGTGCGG | GCCCGGAAGG | 120 |
| TGCCGGCGCT | GGTGCGGGCC | CGGAAGGTGC | AGGCGCTGGT | GCGGGCCCGG | AAGGTGCCGG | 180 |
| CGCTGGTGCG | GGCCCGGAAG | GTGCAGGCGC | TGGTGCGGGC | CCGGAAGGTG | CCGGCGCTGG | 240 |
| TGCGGGCCCG | GAAGGTGCAG | GCGCTGGTGC | GGGCCCGGAA | GGTGCCGGCG | CTGGTGCGGG | 300 |
| CCCGGAAGGT | GCAGGCGCTG | GTGCGGGCCC | GGAAGGTGCC | GGCGCTGGTG | CGGGCCCGGA | 360 |
| AGGTGCAGGC | GCTGGTGCGG | GCCCGGAAGG | TGCCGGCGCT | GGTGCGGGCC | CGGAAGGTGC | 420 |
| AGGCGCTGGT | GCGGGCCCGG | AAGGTGCCGG | CGCTGGTGCG | GGCCCGGAAG | GTGCAGGCGC | 480 |
| TGGTGCGGGC | CCGGAAGGTG | CCGGCGCTGG | TGCGGGCCCG | GAAGGTGCAG | GCGCTGGTGC | 540 |
| GGGCCCGGAA | GGTGCCGGCG | CTGGTGCGGG | CCCGGAAGGT | GCAGGCGCTG | GTGCGGGCCC | 600 |
| GGAAGGTGCC | GGCGCTGGTG | CGGGCCCGGA | AGGTGCAGGC | GCTGGTGCGG | GCCCGGAAGG | 660 |
| TGCCGGCGCT | GGTGCGGGCC | CGGAAGGTGC | AGGCGCTGGT | GCGGGCCCGG | AAGGTGCCGG | 720 |
| CGCTGGTGCG | GGCCCGGAAG | GTGCAGGCGC | TGGTGCGGGC | CCGGAAGGTG | CCCGCATG | 778 |

(2) INFORMATION FOR SEQ ID NO:12:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

| | | | | | |
|---|---|---|---|---|---|
| CGGGCACCTT | CCGGGCCCGC | ACCAGCGCCT | GCACCTTCCG | GGCCCGCACC | AGCGCCGGCA | 60 |
| CCTTCCGGGC | CCGCACCAGC | GCCTGCACCT | TCCGGGCCCG | CACCAGCGCC | GGCACCTTCC | 120 |
| GGGCCCGCAC | CAGCGCCTGC | ACCTTCCGGG | CCCGCACCAG | CGCCGGCACC | TTCCGGGCCC | 180 |
| GCACCAGCGC | CTGCACCTTC | CGGGCCCGCA | CCAGCGCCGG | CACCTTCCGG | GCCCGCACCA | 240 |
| GCGCCTGCAC | CTTCCGGGCC | CGCACCAGCG | CCGGCACCTT | CGGGCCCGC | ACCAGCGCCT | 300 |
| GCACCTTCCG | GGCCCGCACC | AGCGCCGGCA | CCTTCCGGGC | CCGCACCAGC | GCCTGCACCT | 360 |
| TCCGGGCCCG | CACCAGCGCC | GGCACCTTCC | GGGCCCGCAC | CAGCGCCTGC | ACCTTCCGGG | 420 |
| CCCGCACCAG | CGCCGGCACC | TTCCGGGCCC | GCACCAGCGC | CTGCACCTTC | CGGGCCCGCA | 480 |
| CCAGCGCCGG | CACCTTCCGG | GCCCGCACCA | GCGCCTGCAC | CTTCCGGGCC | CGCACCAGCG | 540 |
| CCGGCACCTT | CCGGGCCCGC | ACCAGCGCCT | GCACCTTCCG | GGCCCGCACC | AGCGCCGGCA | 600 |
| CCTTCCGGGC | CCGCACCAGC | GCCTGCACCT | TCCGGGCCCG | CACCAGCGCC | GGCACCTTCC | 660 |
| GGGCCCGCAC | CAGCGCCTGC | ACCTTCGCCG | CCCGCACCAG | CGCCGGCACC | TTCCGGGCCC | 720 |
| GCACCAGCGC | CTGCACCTTC | CGGGCCCGCA | CCAGCGCCGG | CACCCATCGG | ATCG | 774 |

(2) INFORMATION FOR SEQ ID NO:13:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

| | | | | | |
|---|---|---|---|---|---|
| GTGACCTGGA | AAACGAAGTG | GCCCAGCTGG | AAGGGAAGT | TAGATCTCTG | GAAGATGAAG | 60 |
| CGGCTGAACT | GGAACAAAAA | GTCTCGAGAC | TGAAAAATGA | AATCGAAGAC | CTGAAAGCCG | 120 |
| AAATTG | | | | | | 126 |

(2) INFORMATION FOR SEQ ID NO:14:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

| | | | | | |
|---|---|---|---|---|---|
| GTCACCAATT | TCGGCTTTCA | GGTCTTCGAT | TTCATTTTTC | AGTCTCGAGA | CTTTTTGTTC | 60 |
| CAGTTCAGCC | GCTTCATCTT | CCAGAGATCT | AACTTCCCTT | TCCAGCTGGG | CCACTTCGTT | 120 |
| TTCCAG | | | | | | 126 |

(2) INFORMATION FOR SEQ ID NO:15:

(i) SEQUENCE CHARACTERISTICS:
        (A) LENGTH: 126 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GTGACCTGAA AAACAAAGTG GCCCAGCTGA AAAGGAAAGT TAGATCTCTG AAAGATAAAG      60

CGGCTGAACT GAAACAAGAA GTCTCGAGAC TGGAAAATGA AATCGAAGAC CTGAAAGCCA     120

AAATTG     126

(2) INFORMATION FOR SEQ ID NO:16:

(i) SEQUENCE CHARACTERISTICS:
            (A) LENGTH: 126 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GTCACCAATT TTGGCTTTCA GGTCTTCGAT TTCATTTTCC AGTCTCGAGA CTTCTTGTTT      60

CAGTTCAGCC GCTTTATCTT TCAGAGATCT AACTTTCCTT TTCAGCTGGG CCACTTTGTT    120

TTTCAG     126

(2) INFORMATION FOR SEQ ID NO:17:

(i) SEQUENCE CHARACTERISTICS:
            (A) LENGTH: 76 amino acids
            (B) TYPE: amino acid
            (D) TOPOLOGY: linear (ii) MOLECULE TYPE: peptide (xi) SEQUENCE DESCRIPTION: SEQ ID NO:17:

Met Arg Gly Ser His His His His His His Gly Ser Asp Asp Asp Asp
 1               5                  10                  15

Lys Trp Ala Ser Gly Asp Leu Glu Asn Glu Val Ala Gln Leu Glu Arg
            20                  25                  30

Glu Val Arg Ser Leu Glu Asp Glu Ala Ala Glu Leu Glu Gln Lys Val
        35                  40                  45

Ser Arg Leu Lys Asn Glu Ile Glu Asp Leu Lys Ala Glu Ile Gly Asp
    50                  55                  60

His Val Ala Pro Arg Asp Thr Ser Met Gly Gly Cys
65                  70                  75

(2) INFORMATION FOR SEQ ID NO:18:

(i) SEQUENCE CHARACTERISTICS:
            (A) LENGTH: 76 amino acids
            (B) TYPE: amino acid
            (D) TOPOLOGY: linear (ii) MOLECULE TYPE: peptide (xi) SEQUENCE DESCRIPTION: SEQ ID NO:18:

Met Arg Gly Ser His His His His His His Gly Ser Asp Asp Asp Asp
 1               5                  10                  15

Lys Trp Ala Ser Gly Asp Leu Lys Asn Lys Val Ala Gln Leu Lys Arg
            20                  25                  30

Lys Val Arg Ser Leu Lys Asp Lys Ala Ala Glu Leu Lys Gln Glu Val

```
                       35                  40                  45
Ser Arg Leu Lys Asn Glu Ile Glu Asp Leu Lys Ala Lys Ile Gly Asp
        50                  55                  60

His Val Ala Pro Arg Asp Thr Ser Met Gly Gly Cys
 65                  70                  75
```

(2) INFORMATION FOR SEQ ID NO:19:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO:19:

```
Met Arg Gly Ser His His His His His His Gly Ser Asp Asp Asp
 1               5                  10                  15

Lys Ala Ser Tyr Arg Asp Pro Met Gly Ala Gly Ala Gly Ala Gly Pro
                20                  25                  30

Glu Gly Ala Gly Ala Gly Ala Gly Pro Glu Gly Ala Gly Ala Gly Ala
                35                  40                  45

Gly Pro Glu Gly Ala Gly Ala Gly Ala Gly Pro Glu Gly Ala Gly Ala
            50                  55                  60

Gly Ala Gly Pro Glu Gly Ala Gly Ala Gly Ala Gly Pro Glu Gly Ala
 65                  70                  75                  80

Gly Ala Gly Ala Gly Pro Glu Gly Ala Gly Ala Gly Ala Gly Pro Glu
                85                  90                  95

Gly Ala Gly Ala Gly Ala Gly Pro Glu Gly Ala Gly Ala Gly Ala Gly
                100                 105                 110

Pro Glu Gly Ala Arg Met Pro Thr Ser Trp
        115                 120
```

(2) INFORMATION FOR SEQ ID NO:20:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
GGTGACCTGA AAACAAAGT  GGCCCAGCTG AAAAGCAAAG TTAGATCTCT GAAAGATAAA      60
GCGGCTGAAC TGAAACAAGA AGTCTCGAGA CTGGAAAATG AAATCGAAGA CCTGAAAGCC     120
AAA                                                                   123
```

(2) INFORMATION FOR SEQ ID NO:21:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GGTGACCTGG AAAACGAAGT GGCCCAGCTG GGAAGGGAAG TTAGATCTCT GGAAGATGAA      60
GCGGCTGAAC TGGAACAAAA AGTCTCGAGA CTGAAAAATG AAATCGAAGA CCTGAAAGCC     120
```

```
GAA                                                                                       123
```

(2) INFORMATION FOR SEQ ID NO:22:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:22:

```
Arg Gly Asp Ser
 1
```

(2) INFORMATION FOR SEQ ID NO:23:

(i) SEQUENCE CHARACTERISTICS:
        (A) LENGTH: 308 amino acids
        (B) TYPE: amino acid
        (D) TOPOLOGY: linear (ii) MOLECULE TYPE: Protein (ix) FEATURE:
        (A) NAME/KEY: Other
        (B) LOCATION: 1...8
        (D) OTHER INFORMATION: where any of the first set starting at
            positions 1 through 8 may be absent or present (ix) FEATURE:
        (A) NAME/KEY: Other
        (B) LOCATION: 9...20
        (D) OTHER INFORMATION: where amino acids shown at
            positions 9 through 20 are Pro Glu Gly (ix) FEATURE:
        (A) NAME/KEY: Other
        (B) LOCATION: 21...308
        (D) OTHER INFORMATION: where any of the subsets starting at
            position 21 through 308 may be absent or present (xi) SEQUENCE DESCRIPTION: SEQ ID NO:23:

```
Ala Gly Ala Gly Ala Gly Ala Gly Pro Glu Gly Pro Glu Gly Pro Glu
 1               5                  10                  15

Gly Pro Glu Gly Pro Glu Gly Pro Glu Gly Pro Glu Gly Pro Glu Gly
                20                  25                  30

Pro Glu Gly Pro Glu Gly Pro Glu Gly Pro Glu Gly Pro Glu Gly Pro
                35                  40                  45

Glu Gly Pro Glu Gly Pro Glu Gly Pro Glu Gly Pro Glu Gly Pro Glu
     50                  55                  60

Gly Pro Glu Gly Pro Glu Gly Pro Glu Gly Pro Glu Gly Pro Glu Gly
 65                  70                  75                  80

Pro Glu Gly Pro Glu Gly Pro Glu Gly Pro Glu Gly Pro Glu Gly Pro
                85                  90                  95

Glu Gly Pro Glu Gly Pro Glu Gly Pro Glu Gly Pro Glu Gly Pro Glu
               100                 105                 110

Gly Pro Glu Gly Pro Glu Gly Pro Glu Gly Pro Glu Gly Pro Glu Gly
         115                 120                 125

Pro Glu Gly Pro Glu Gly Pro Glu Gly Pro Glu Gly Pro Glu Gly Pro
         130                 135                 140

Glu Gly Pro Glu Gly Pro Glu Gly Pro Glu Gly Pro Glu Gly Pro Glu
145                 150                 155                 160

Gly Pro Glu Gly Pro Glu Gly Pro Glu Gly Pro Glu Gly Pro Glu Gly
```

-continued

```
                165                 170                 175
Pro Glu Gly Pro Glu Gly Pro Glu Gly Pro Glu Gly Pro
                    180                 185                 190
Glu Gly Pro Glu Gly Pro Glu Gly Pro Glu Gly Pro Glu
        195                 200                 205
Gly Pro Glu Gly Pro Glu Gly Pro Glu Gly Pro Glu Gly
        210                 215                 220
Pro Glu Gly Pro Glu Gly Pro Glu Gly Pro Glu Gly Pro
225                 230                 235                 240
Glu Gly Pro Glu Gly Pro Glu Gly Pro Glu Gly Pro Glu
                245                 250                 255
Gly Pro Glu Gly Pro Glu Gly Pro Glu Gly Pro Glu Gly
            260                 265                 270
Pro Glu Gly Pro Glu Gly Pro Glu Gly Pro Glu Gly Pro
            275                 280                 285
Glu Gly Pro Glu Gly Pro Glu Gly Pro Glu Gly Pro Glu
        290                 295                 300
Gly Pro Glu Gly
305
```

(2) INFORMATION FOR SEQ ID NO:24:

(i) SEQUENCE CHARACTERISTICS:
        (A) LENGTH: 700 amino acids
        (B) TYPE: amino acid
        (D) TOPOLOGY: linear (ii) MOLECULE TYPE: Protein (ix) FEATURE:
        (A) NAME/KEY: Other
        (B) LOCATION: 1...22
        (D) OTHER INFORMATION: where Xaa at positions 1, 8, 15, and 22
            may be any one of Ala, Gly, Ile, Leu, Met, Phe, Pro, Trp,
            or Val (ix) FEATURE:
        (A) NAME/KEY: Other
        (B) LOCATION: 2...23
        (D) OTHER INFORMATION: where Xaa at positions 2, 9, 16, and 23
            may be any amino acid (ix) FEATURE:
        (A) NAME/KEY: Other
        (B) LOCATION: 3...24
        (D) OTHER INFORMATION: where Xaa at positions 3, 10, 17, and 24
            may be any amino acid (ix) FEATURE:
        (A) NAME/KEY: Other
        (B) LOCATION: 4...25
        (D) OTHER INFORMATION: where Xaa at positions 4, 11, 18, and 25
            may be any one of Ala, Gly, Ile, Leu, Met, Phe, Pro, Trp,
            or Val (ix) FEATURE:
        (A) NAME/KEY: Other
        (B) LOCATION: 5...26
        (D) OTHER INFORMATION: where Xaa at positions 5, 12, 19, and 26
            may be any one of Asn, Cys, Gln, Thr, Val, Lys, His, Glu,
            Asp, Arg, or Ser (ix) FEATURE:
        (A) NAME/KEY: Other
        (B) LOCATION: 6...27
        (D) OTHER INFORMATION: where Xaa at positions 6, 13, 20, and 27
            may be any amino acid (ix) FEATURE:

(A) NAME/KEY: Other
(B) LOCATION: 7...28
(D) OTHER INFORMATION: where Xaa at positions 7, 14, 21, and 28 may be any one of Asn, Cys, Gln, Thr, Val, Lys, His, Glu, Asp, Arg, or Ser (ix) FEATURE:
(A) NAME/KEY: Other
(B) LOCATION: 29...308
(D) OTHER INFORMATION: where Xaa in any subset from positions 29 through 308 may be absent or present (xi) SEQUENCE DESCRIPTION: SEQ ID NO:24:

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
 130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa
 210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350
```

```
Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa
            610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa
            690                 695                 700
```

REVERSIBLE HYDROGELS

BACKGROUND OF THE INVENTION

The invention relates to a class of block copolymers that form solutions that can reversibly gel under specific conditions.

Gels are polymer networks that can absorb solvents and thereby swell. For example, hydrogels are gels that swell in aqueous solutions. In general, gels fall into two categories. In crosslinked gels, the polymer chains that make up the networks are covalently bonded to each other. In physical gels, the polymer chains are attracted to each other by non-covalent forces (e.g., ionic, electrostatic, and/or van der Waals interactions).

Because the polymer chains of a physical gel are not chemically crosslinked, physical gels can have special properties. For example, physical gels can be highly responsive to physical stimuli such as temperature, pH, ion concentration, solvent polarity, or polymer concentration. The responsiveness can be manifest as swelling or shrinkage of the gel, changes in the shape of the gel, or changes in the viscosity of the gel. The gel can also undergo a reversible phase change between its gel and liquid states under appropriate conditions.

A class of physical gels that are of particular interest are the monodisperse gels. Monodisperse gels are made up of identical polymer chains of uniform size. Because each chain is of the same molecular weight, the spacing between structural elements is also of generally uniform size. By appropriate design, more direct control of pore size can be achieved in a monodisperse polymer system relative to a polydisperse system.

SUMMARY OF THE INVENTION

The invention is based on the discovery that a synthetic block copolymer that includes α-helical blocks, e.g., terminal blocks, which form intermolecular coiled-coil structures, and one or more random-coil blocks, which link the α-helical blocks, can form suspensions that can reversibly gel to form monodisperse hydrogels. The transition between the gel and liquid phases depends on pH, temperature, concentration, and chemical structure. The copolymers can be synthesized chemically and biologically, e.g., through genetic engineering.

One embodiment of the invention features a synthetic block copolymer XYZ. The block copolymer XYZ includes two α-helical protein blocks X and Z, each having an amino acid sequence and conformation that allow each α-helical protein block to form a coiled-coil with an α-helical protein block on another block copolymer XYZ; and a water-soluble, random-coil protein block Y, the random-coil protein block covalently linking the two α-helical protein blocks. For example, the first α-helical block, the random-coil block, and the second α-helical block can form a continuous peptide chain. Optionally, other amino acid sequences such as β-sheet or turn sequences can be included in the peptide chain, either at the ends of the chain or between the other blocks (e.g., between the α-helical and random-coil blocks).

Another embodiment of the invention features a synthetic block copolymer having at least two α-helical protein blocks, each having an amino acid sequence and conformation that allow each α-helical protein block to form a coiled-coil with an α-helical protein block on another molecule of the block copolymer; and at least one water-soluble, random-coil protein block, the random-coil protein block linking at least two of the α-helical protein blocks.

The random-coil block Y can have the sequence $[(AlaGly)_p ProGluGly]_n$ (SEQ ID NO: 23), where p is 0 to 4 (e.g., 1, 2, or 3) and n is 5 to 100 (e.g., 8 to 54).

The sequences of amino acids that make up X and Z have an $(ABCDEFG)_m$ (SEQ ID NO: 24) pattern, where m is 4 to 100 (e.g., 6 to 18); A and D are hydrophobic amino acids; E and G are polar amino acids; and B, C, and F can be any amino acid. In some cases, more than 80% of the E and G amino acids in X and Z are acidic amino acids. In other cases, more than 80% of the E and G amino acids in X and Z are basic amino acids. Alternatively, more than 80% of the E and G amino acids of X can be acidic amino acids while more than 80% of the E and G amino acids of Z can be basic amino acids. In another alternative, more than 80% of the E amino acids of X and G amino acids of Z can be acidic amino acids while more than 80% of the E amino acids of Z and G amino acids of X can be basic amino acids. In still another alternative, more than 80% of the E amino acids of X and Z can be acidic amino acids while more than 80% of the G amino acids of X and Z can be basic amino acids.

More than 80% of the D amino acids of X and Z can be leucine, for example, or trifluoroleucine.

The block copolymer can also include linker proteins that link the α-helical protein blocks to the random-coil block protein.

In some cases, X and Z are at least 90% identical to each other. X and Z can be non-identical.

The block copolymer can also include a recognition element that specifically binds to a cell (e.g., a fibroblast) or to a macromolecule (i.e., the element binds preferentially to the target cell or molecule in a sample including the target, but does not bind to other cells or molecules in the sample). Examples of such recognition elements include the heparin-binding domain, the endothelial-binding domain, or the sequence ArgGlyAsp. The recognition element is generally continuous with the peptide chain that makes up the copolymer, and can be incorporated either within the random-coil block, between separate blocks (e.g., linking the α-helical block and the random-coil block), or at an end of the peptide sequence. Alternatively, the recognition element can be bound to the copolymer via hydrophobic interactions, electrostatic interactions, disulfide bonds, or hydrogen bonds.

The invention also features a gel that includes a liquid (e.g., an aqueous liquid such as water) and a block copolymer suspended in the liquid. The suspension can be monodisperse.

In another aspect, the invention features a method for making a block copolymer. The method includes the steps of obtaining host cells including an expression vector having a DNA sequence that encodes the amino acid sequence of the block copolymer; culturing the host cells under conditions and for a time sufficient to express the block copolymer; and isolating the block copolymer from the host cells.

Yet another embodiment of the invention is a method of using a block copolymer to stimulate regeneration of tissue around a wound. The method includes the steps of dissolving the copolymer in a liquid to form a solution, and treating the wound with the solution to form a gelatinous scaffold for tissue regeneration.

Still another embodiment of the invention is a wound dressing that includes a block copolymer and an antibiotic compound (e.g., bacitracin, neosporin, erythromycin), where the copolymer and the antibiotic are both dissolved in a liquid.

In another aspect, the invention features nucleic acids encoding the new block copolymers. Examples of suitable nucleic acids can include the following sequences:

```
GGT GAC CTG GAA AAC GAA GTG GCC CAG CTG GGA AGG GAA
GTT AGA TCT CTG GAA GAT GAA GCG GCT GAA CTG GAA CAA
AAA GTC TCG AGA CTG AAA AAT GAA ATC GAA GAC CTG AAA
GCC GAA (SEQ ID NO:21); and GGT GAC CTG AAA AAC AAA GTG GCC CAG CTG AAA AGC AAA
GTT AGA TCT CTG AAA GAT AAA GCG GCT GAA CTG AAA CAA
GAA GTC TCG AGA CTG GAA AAT GAA ATC GAA GAC CTG AAA
GCC AAA (SEQ ID NO:20).
```

The invention also features a vector that includes this nucleic acid operatively linked to a promoter. As used herein, the term "operatively linked" means that selected DNA, e.g., encoding the copolymers, is in proximity with a promoter, e.g., a tissue-specific promoter, to allow the promoter to regulate expression of the selected DNA. In addition, the promoter is located upstream of the selected DNA in terms of the direction of transcription and translation. Suitable promoters include the $P_{lac}$ promoter, the T5 promoter, the adenovirus major late promoter, early and late promoters of SV40, CMV promoter, TH promoter, RSV promoter, or B19p6 promoter (Shad et al., *J. Virol.*, 58:921, 1986). The promoter may additionally include enhancers or other regulatory elements.

The invention also features a host cell (e.g., a prokaryote such as *E. coli* or other bacteria, or a eukaryote such as a fungus, e.g., yeast).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, manufacturers' technical information, and other references mentioned herein are incorporated by reference in their entirety. In case of conflict, the present application, including definitions, will control. In addition, the materials, methods, and examples are illustrative only and not intended to be limiting.

The new polymers have numerous advantages over many existing gel-forming polymers. For example, since any given batch of the new polymers can be produced biologically from a single template, virtually all of the molecules in that batch will be of equal size; gels formed by intermolecular binding of the α-helical blocks are therefore monodisperse. Monodisperse gels have a uniform pore size that typically depends on the length of the random-coil block.

Standard molecular biological techniques (e.g., automated DNA synthesis) allow any amino acid sequence to be encoded by a gene and expressed in vivo. These techniques enable many characteristics of the new polymers, and therefore of the new suspensions, to be precisely controlled. Examples of the characteristics that can be controlled include: the lengths of the helical and random-coil blocks, the hydrophilicity or hydrophobicity of any of the blocks, the pore size of the gels formed from the polymer suspensions, and the responsiveness of the gels to pH and temperature changes.

Microorganisms can synthesize, in relatively large quantities, high molecular weight materials that are inherently stereoregular, monodisperse, and of controlled sequence. Stereoregularity and monodispersity are rarely achieved by conventional methods of polymerization such as step, chain, ring-opening, and coordination methods. Biosynthetic polymers, on the other hand, can exhibit both of these advantages, and the degree of structural control afforded by biosynthesis extends to the secondary, tertiary, and quaternary levels. The physical properties associated with these biomaterials can be developed on the bases of shape, hydrophilic/hydrophobic character, and charge placement. Moreover, designing and synthesizing polymeric materials biosynthetically allows control over the structure of the materials on both the microscopic and macroscopic levels.

Additionally, a recognition sequence or other peptidic target sequence can advantageously be inserted into, for example, the random-coil blocks of the new block copolymers by splicing a gene encoding that sequence into the template for the new copolymers. The splicing procedure can simply involve digestion of the template with a restriction enzyme followed by ligation with the gene encoding the sequence. Gels having an integral target sequence can be used, for example, in affinity chromatography.

Yet another advantage of the new copolymers is that they have relatively low molecular weight when compared to many other gel-forming molecules. Their low molecular weight can result in decreased viscosity of solutions of the copolymers while still affording high viscosity gels under suitable conditions.

Other features and advantages of the invention will be apparent from the following detailed description, and from the claims.

BRIEF DESCRIPTION OF THE DRAWINGS

FIGS. 6A and 6B are representations of the sequences of coding (5'-3') and noncoding (3'-5') DNA for linkers L1 and L2, respectively.

FIG. 8 is a representation of the sequence of synthetic DNA encoding [(AG)$_3$PEG]$_{10}$ (SEQ ID NOS: 9,10) inserted into the NruI and SphI restriction sites.

FIG. 9 is a representation of the sequence of synthetic DNA encoding for [(AG)$_3$PEG]$_{28}$ (SEQ ID NOS: 11,12) inserted into the NruI and SphI restriction sites.

FIGS. 10A and 10B are representations of the sequence of synthetic DNA encoding the acidic leucine zipper and the sequence of synthetic DNA encoding the basic leucine zipper, respectively, inserted into BstEII restriction sites.

DETAILED DESCRIPTION

Figure 1A:
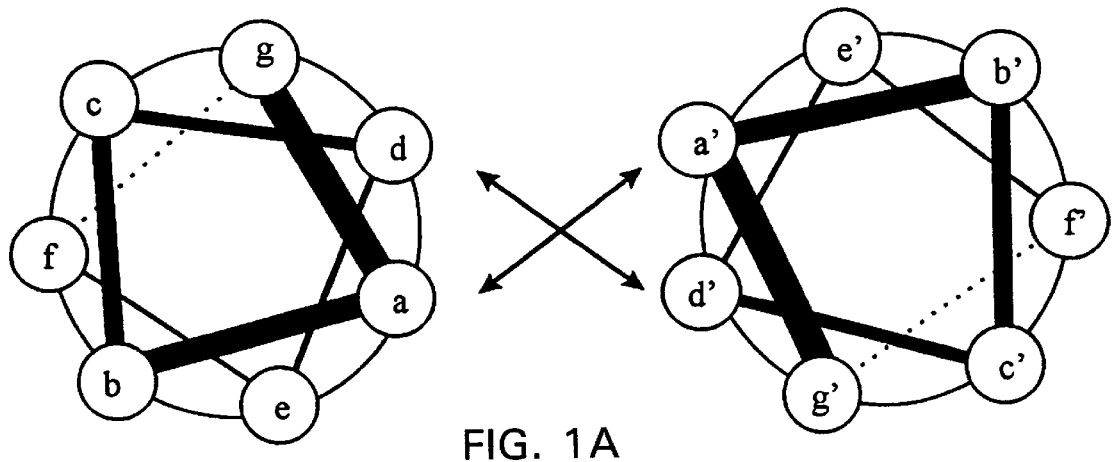
FIGS. 1A and 1B are helical wheel representations of coiled-coil structures.

A new class of block copolymers is disclosed. The new copolymers combine the properties of coiled-coil leucine zipper proteins with the properties of flexible, water-soluble, random-coil proteins. Aggregation of the new copolymers forms three-dimensional, monodisperse gel networks that are responsive to changes in pH, solvent, and temperature.

Description of the Proteins

The structural complexity of a protein in solution or in the solid state depends on the chemical nature of both the protein and its environment. Variables such as pH, temperature, concentration, and chemical structure can influence the types of conformations that polymers adopt in solution. Favorable or unfavorable solvent-polymer interactions can also contribute to the overall conformation of the protein. For example, unfavorable solvent-polymer interactions can cause protein chains to contract to exclude solvent, to aggregate, and to precipitate. The correlation between conformations existing in natural polypeptides and their amino acid periodicity form the basis for rational materials design.

The block copolymers of the invention have α-helical blocks, generally separated by random-coil domains. Other protein blocks (e.g., β-sheets and turns) can also be included in the copolymers, bewteen the α-helical blocks or the random-coil blocks, or both. The proteins can be used, for example, to make reversible three-dimensional gel networks, in which physical aggregates of two or more helical chains form the junction points of the gel and the random-coil domains control swelling of the gel. The molecular weight, stereoregularity, sequence, and function of the new proteins can be concurrently controlled. The block copolymers with α-helical and random-coil domains disclosed herein can form monodisperse gels.

α-Helical Blocks—Coiled-coils

Certain natural polypeptides (e.g., keratin) can adopt α-helical conformations. The axes of individual helices themselves pursue a helical course to form multistranded cables, or "coiled-coils," probably due to repeating sequences of amino acids; a seven amino acid repeat, (a b c d e f g)$_n$(SEQ ID NO: 24), defines a coiled-coil (see FIGS. 1A and 1B). Proteins having coiled-coil domains are also called "leucine zipper" proteins, because leucine residues often occur in the a and d positions of natural helices. In general, a and d are hydrophobic amino acids that facilitate and stabilize interchain association of α-helices by forming complementary hydrophobic helical faces that interact through hydrophobic and van der Waals interactions.

In addition to the hydrophobic core formed by the a and d residues in 7$_2$ α-helices (i.e., having two turns per seven amino acid residues), the formation of coiled-coils can be further modulated by interactions between regularly spaced charged groups at specific positions in the general heptad repeat. Thus, for example, the stabilization of the coiled-coil helices can be enhanced or diminished in synthetic peptides by positioning attractive or repulsive charged groups at e and g positions. Polypeptides can be designed to have the propensity to form parallel or antiparallel coiled-coils based on charge—charge interactions between the amino acids in the e and g positions on adjacent helices. In designing coiled-coil domains, it can be useful to incorporate hydrophilic amino acids such as Thr, Ser, and Cys at positions b, c, and f to increase solubility. The seven amino acid units repeat a minimum of four times to form a 7$_2$ α-helical structure.

Figure 1B:
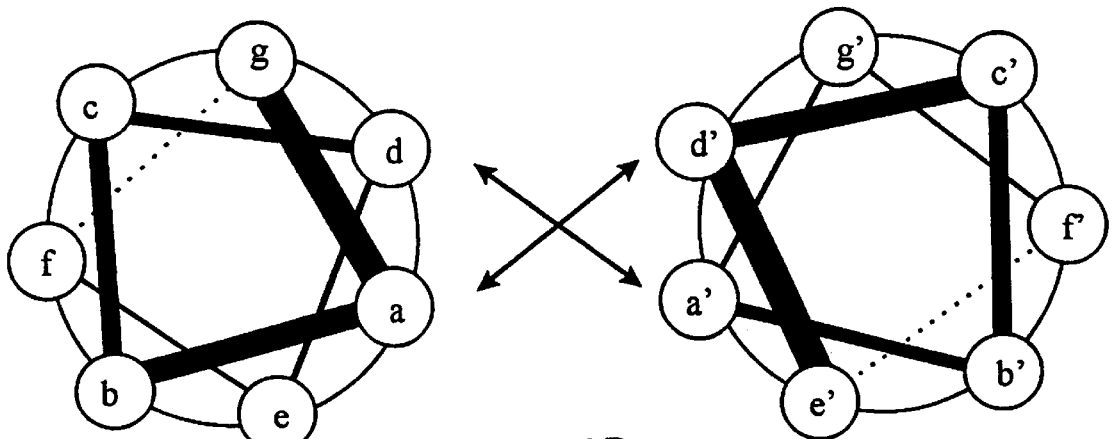

Parallel and antiparallel arrangements of two leucine zippers are best illustrated by considering the general positions of residues that are in proximity to each other. In a coiled-coil structure, positions a and d of two 7$_2$ helices are associated at the interface and intertwine to form a coiled-coil structure with a slight left-handed twist. General representations of parallel and anti-parallel dimers of two α-helical leucine zippers are shown in FIGS. 1A and 1B, wherein one chain is denoted by a general heptad repeat (a b c d e f g)$_n$(SEQ ID NO: 24), and the other by (a' b' c' d' e' f' g')$_n$(SEQ ID NO: 24). FIG. 1A is a representation of a parallel coiled-coil viewed down the helical axes from the NH$_2$-termini of both strands. In the parallel coiled-coil configuration, the amino acid side chains in the d and a' positions interact with each other (e.g., those hydrogen bonds or electrostatic interactions), as do those in the a and d' positions. FIG. 1B is a representation of an antiparallel coiled-coil viewed down the helical axes from the NH$_2$-terminus of the left strand and the COOH-terminus of the right strand. In the antiparallel arrangement, the amino acid side chains in the a and a' positions interact with each other, as do those in the d and d' positions. Interhelical hydrophobic interactions are present between the a, a', d, and d' groups whereas the e, e', g, and g' form electrostatic interhelical interactions.

In addition to those α-helical blocks described in detail above, there are many other α-helical blocks that form coiled-coils and would thus be suitable for use with the present invention. Examples include natural transcription factor proteins such as Fos, Jun, C/EBP, CREB, and GCN4; natural muscle and structural proteins such as tropomyosin, myosin, paramyosin, streptococcal M-protein, and desmoplakin; and other miscellaneous protein fragments such as *S. cerevisiae* heat shock transcription factor (HSF), fibrinogen, laminin, tenascin, macrophage scavenger receptor protein, bacteriophage leg fiber protein, α-actinin, dystrophin, ColE1 Rop protein, tobacco mosaic virus coat protein, regions of the influenza virus haemagglutinin glycoprotein, and derivative and analogs of any of these proteins. Still other suitable examples can be found in Cohen et al., *Proteins: Structure, Function, and Genetics*, 7:1 (1990).

In addition to forming dimers, leucine zippers are also known to form trimeric and tetrameric aggregates. These higher order aggregate states are referred to as multiple-helix bundles instead of coiled-coils. Coiled-coils generally contain a narrow hydrophobic surface whereas multiple helix bundles have a wide hydrophobic surface. The latter surface involves additional hydrophobic residues in the packing arrangement. The conformation of the core amino acid side chains determines whether a two-, three-, or four-stranded oligomerization state will predominate.

The stabilization of coiled-coils can be modulated by both intra- and interhelical electrostatic interactions. Attractive or repulsive interactions along the helix affect the stability of an individual α-helix as well as the state of association of multiple helices.

Random Coil Blocks

In the present invention, the random coil block has the structure $[(AG)_p PEG]_n$ (SEQ ID NO: 23), where p is 0 to 4 and n is 5 to 100. However, nearly any sequence that does not form an α-helical or β-sheet structure can be used. Such amino acid sequences do not have an inherent higher order structure, and are thus described as random coil blocks in the present context.

Particularly suitable as random coil blocks are sequences that have ionizable side chains since these side chains are easily hydrated and afford the desired gelation properties. Nevertheless, it can be desirable to have few ionizable side chains if the goal is to form gels in less polar solvents, such as diethyl ether.

Preparation of the Proteins

The production of genetically synthesized materials generally begins with the insertion of a piece of DNA (e.g., chemically synthesized, or isolated, or derived from a natural source) into a circular cloning vector through a series of cutting and ligating reactions. The DNA encodes a specific sequence of amino acids.

Once the DNA sequence is verified, this piece of DNA is cut from the cloning vector and inserted into an expression vector or plasmid that allows for protein production in a prokaryotic or eukaryotic host microorganism such as a bacterium (e.g., *E. coli*) or a yeast (e.g., *S. cerevisiae*). The microorganism can then be grown, thereby initiating production of the protein. After an allotted amount of time (i.e., 1 to 5 hours, preferably about 3 hours), the proteins are isolated, purified, and characterized. If the protein is not secreted by the microorganism, the cells can be lysed to facilitate protein isolation.

In the new copolymers, α-helical and random-coil proteins are combined in a single chain to impart both rigidity, through the helical segment, and flexibility, through the coiled segment. The general design of the copolymer can be, for example, a helix-coil-helix motif, XYZ, where the helices X and Z are leucine zippers. However, other block copolymers having at least two α-helical blocks and at least one random-coil block are also contemplated. For example, a copolymer having repeating [helix-coil] motif can be suitable. The helical end blocks recognize and associate with each other through interchain hydrophobic and electrostatic interactions. The random-coil domains, Y, act as flexible water-soluble spacers inserted between these ends.

Figure 11:
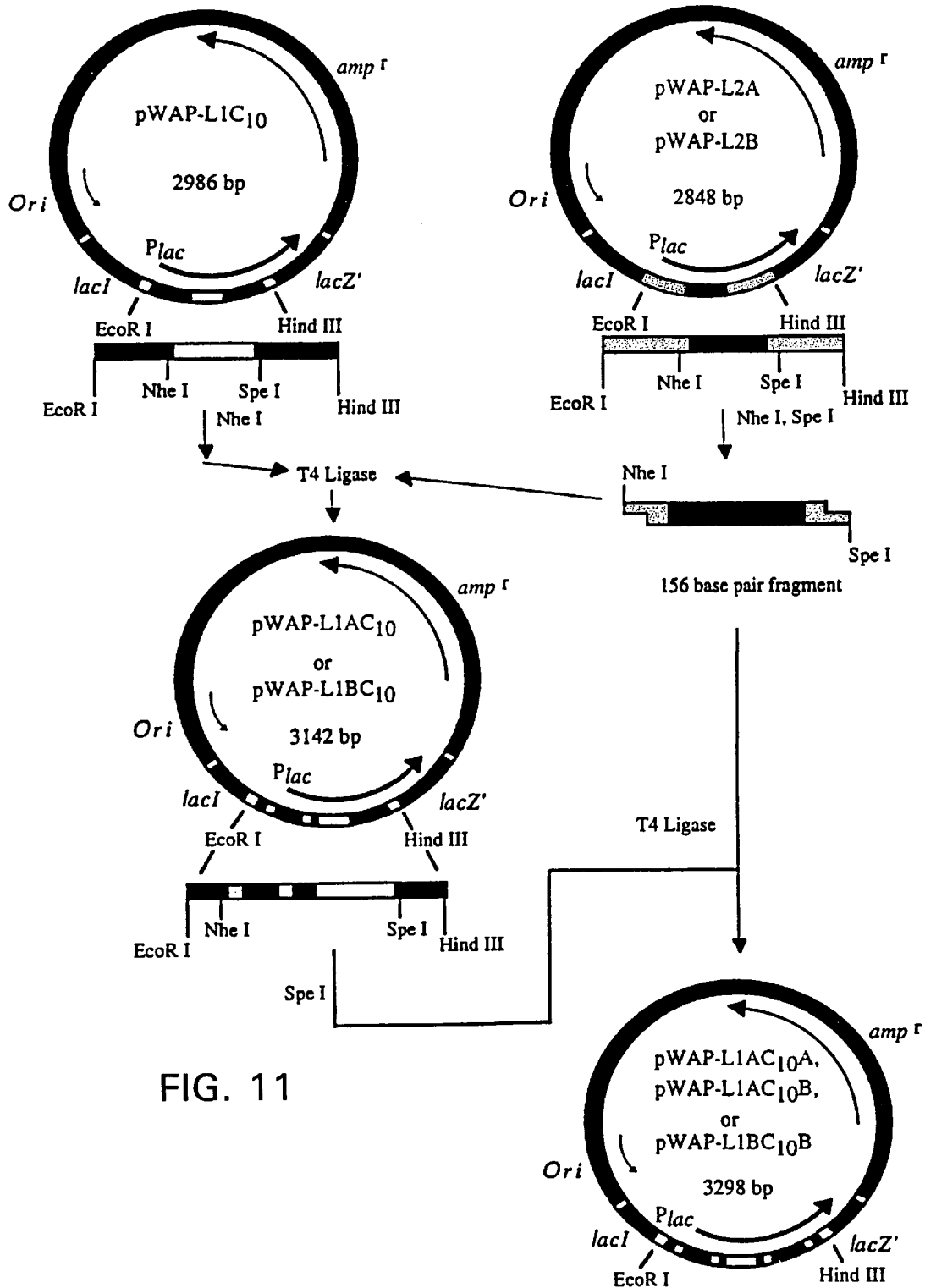
FIG. 11 is a schematic diagram strategy for cloning artificial genes encoding a helix-coil-helix into pWAP-LIC$_{10}$.
Figure 12:
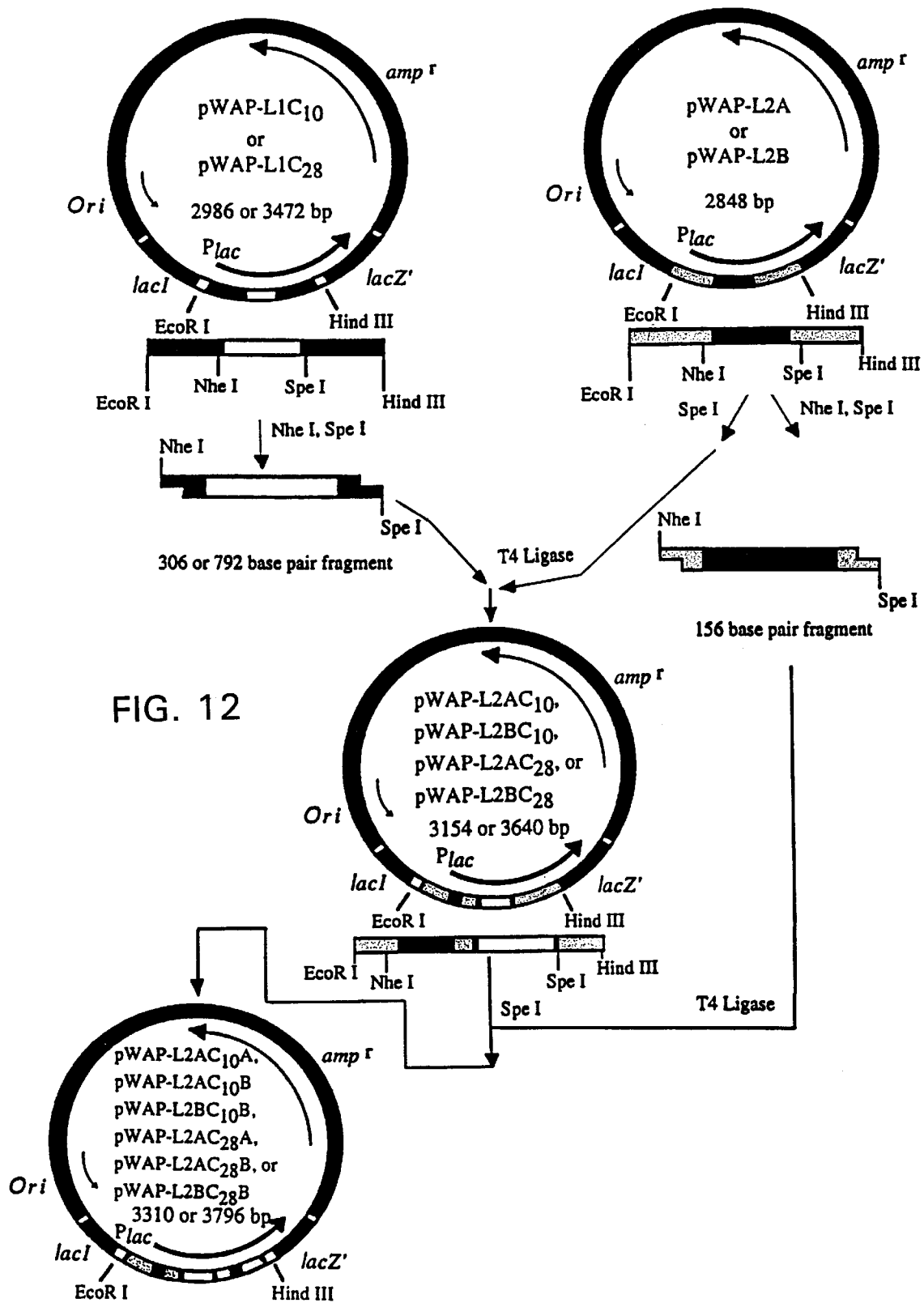
FIG. 12 is a schematic diagram of an alternate strategy for cloning artificial genes encoding a helix-coil-helix into pWAP-LIC2A and pWAP-LIC2B.
Figure 13:
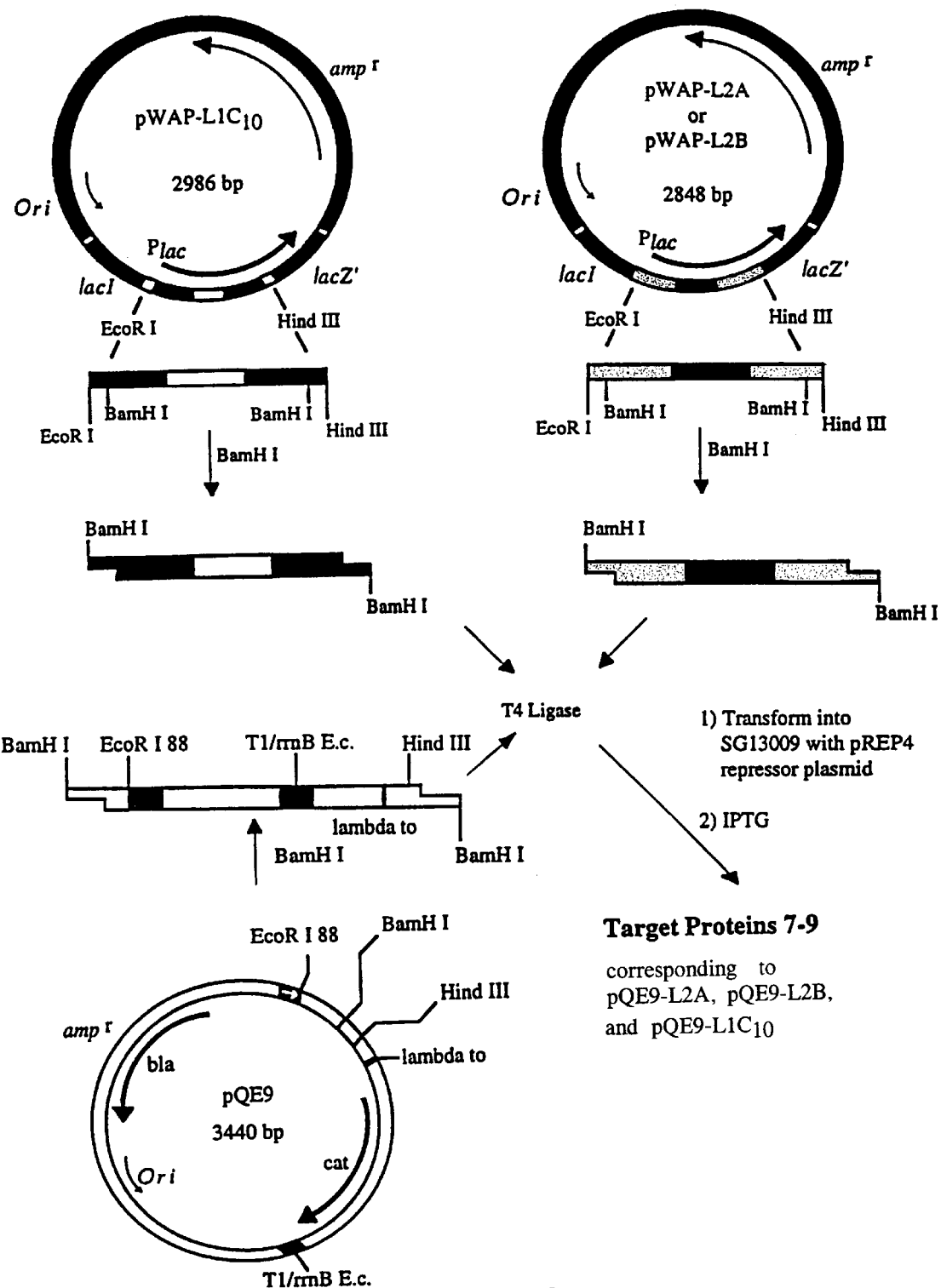
FIG. 13 is a schematic diagram of a strategy for expressing artificial genes encoding a helix or a coil in Qiagen pQE9 plasmid DNA.
Figure 14:
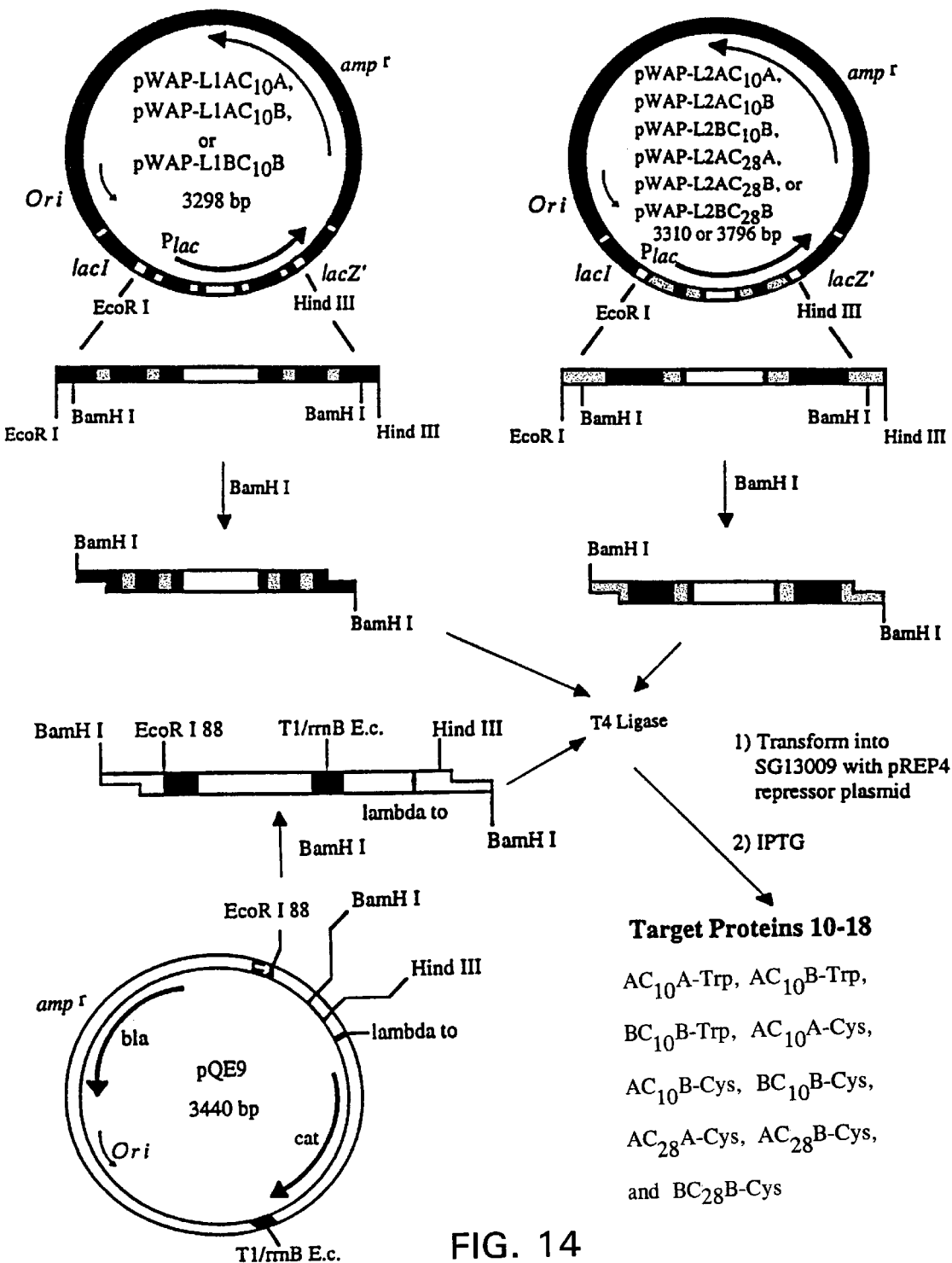
FIG. 14 is a schematic diagram of a strategy for expressing artificial genes encoding a helix-coil-helix in Qiagen pQE9 plasmid DNA.

The formation of the helix-coil-helix copolymers as a single chain generally proceeds as follows. Two separate pieces of DNA are chemically synthesized to incorporate the sequences encoding the random coil and the helical blocks, individually (see FIG. 7, for example), each flanked by restriction sites. By digesting the pieces of DNA with the appropriate restriction enzymes, then ligating the digestion products, fragments encoding triblocks (or higher multi-block copolymers) can be assembled. Two examples of triblock formation are shown in FIGS. 11 and 12. As shown in FIG. 13, the blocks of the triblock-encoding sequences can be inserted into an expression vector by digesting with a restriction enzyme that cuts both at an insertion site in the vector and at the ends of the triblock-encoding sequence. Multiblock-encoding sequences could similarly be ligated into the vector (FIG. 14). Examples of multiblock copolymers can also have a repeated helix-coil motif, as in helix-coil-helix-coil-helix-coil. Additionally, nucleic acids encoding other amino acid sequences such as β-sheets, turns, and recognition sequences that bind specifically to macromolecules or cells can be ligated into the vector. Moreover, although the nucleic acids encoding the various blocks of the copolymers can be ligated into a single vector (i.e., allowing the entire block copolymer to be expressed as a single, continuous peptide chain), the individual blocks can alternatively be encoded by nucleic acids in vectors in separate host cells. In this case, the blocks can be covalently linked to each other by standard methods (i.e., after the protein blocks are expressed by the respective host cells) to form the complete copolymers.

Gelation

The new polymers spontaneously self-organize into well-defined, supramolecular networks under a given set of conditions (e.g., generally 10–45° C., pH 6–10). The networks can be designed to gel at a given pH by changing the charge pattern at the e and g positions of the helix. For example, more acidic side chains in these positions would cause the networks to gel at lower pH. The terminal helices aggregate to produce a three-dimensional network, while the flexible intervening random-coil segment retains solvent and prevents precipitation of the chain. The result is a gel that is reversibly responsive to both pH and temperature changes. The reversibility of gelation results from the destabilizing effects of pH and temperature on the electrostatic and hydrophobic interactions of the helical ends.

Gels having melting temperatures ($T_m$) over 37° C. can be of particular interest, since the use of gels formed from the new proteins as delivery vehicles in or on the body will require that the gels are stable at body temperature. The melting temperature depends on the amount of energy that must be supplied to the polymeric network to disrupt the non-covalent bonds (e.g., ionic and van der Waals interactions) that determine the three-dimensional conformation of the proteins and maintain the integrity of the gel. The energy required depends on the unique amino acid sequence and coiled-coil design. The protein unfolds at elevated temperatures, but returns to the low-energy α-helical folded arrangement upon cooling, thereby enabling coiled-coils to form again.

Figure 2:
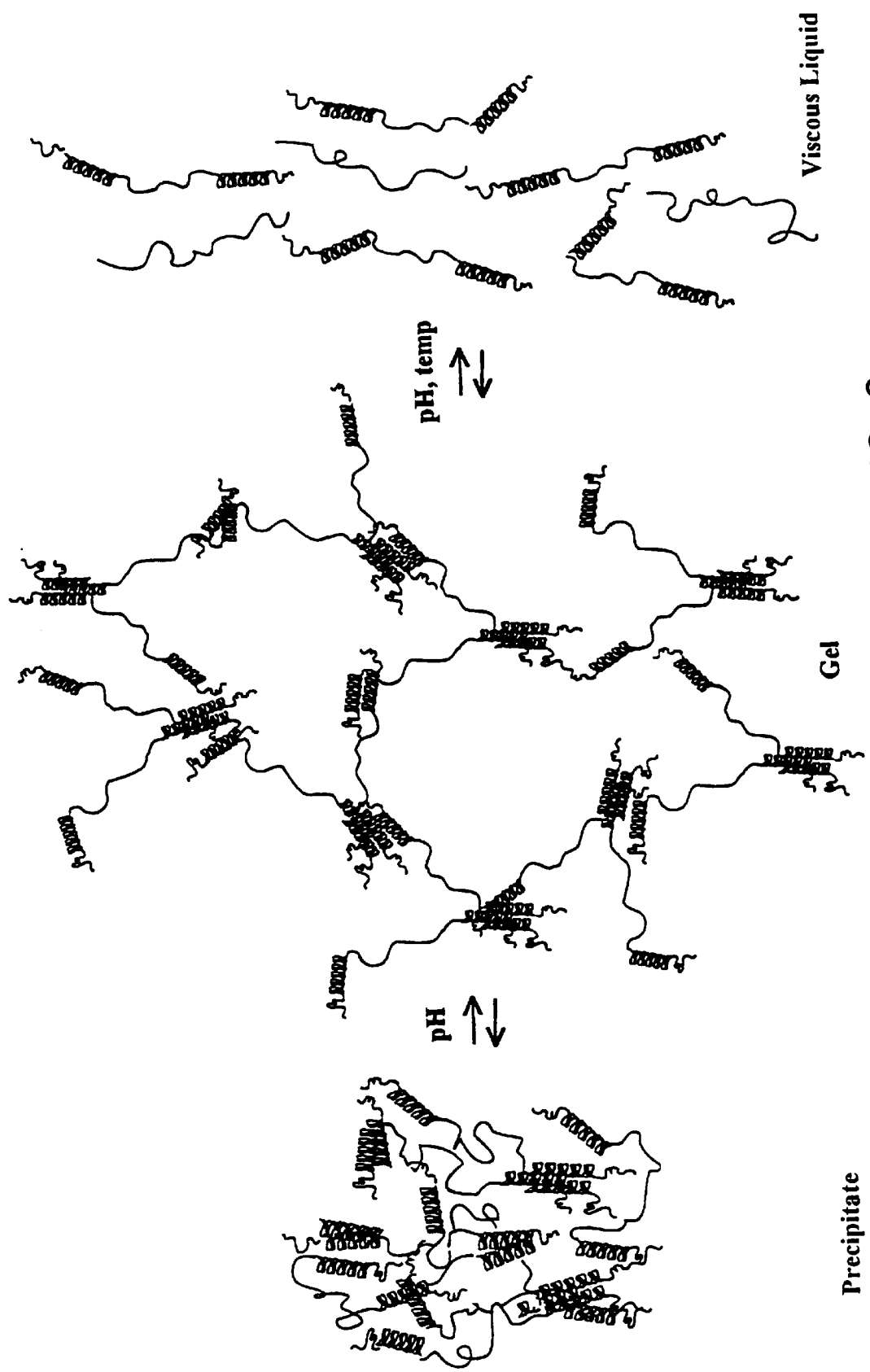
FIG. 2 is a general schematic of the physical gelation process of a monodisperse triblock copolymer.

If protein chains with many acidic residues and relatively few basic residues are suspended in a low pH solution, the sidechain acidic groups can become protonated, resulting in increased stability of the coiled-coil regions. The proteins would be likely to precipitate from the solution because highly associated oligomer states of the helical domains can be formed. The random-coil domain would also have protonated acidic groups that would cause it to collapse to a hydrophobically packed globule. As the pH of the solution is increased, deprotonation of the acidic residues in the random-coil domain can result in swelling of the flexible spacer; moderate deprotonation of the acidic groups in the helical domain does not disrupt the helical—helical packing. The protein therefore behaves as a noncovalent, gelled network. At still higher pH, the acidic residues in the helical domains also become deprotonated, thus creating repulsive charge—charge interactions between the helices; as a result, the chains are free to slip past one another. This proposed gelation process is depicted in a general schematic in FIG. 2.

An illustrative example is provided by the $AC_{10}A$, $AC_{10}B$, and $BC_{10}B$ block copolymers described below in Example 1. In this example, A is an acidic α-helical block, B is a basic α-helical block, and $C_{10}$ is a random-coil block. $AC_{10}A$ precipitates from aqueous solutions at pH values lower than 6, is a gel between pH 6 and 9.5, and forms a homogeneous solution at pH values over 9.5. $AC_{10}B$'s phase transitions are shifted to higher pH values, having a gel phase from pH 7 to 10. $BC_{10}B$ is a gel only at pH values above 9. Thus, a correlation is observed: the more basic residues that are incorporated into the α-helical blocks, the higher the pH required for both gelation and dissolution.

Hydrogels belong to a class of functional materials that respond to a variety of stimuli in aqueous environments. They can be designed to swell or shrink under certain physiological conditions (e.g., at high or low salt concentration, pH, or temperature) and they can be used to encapsulate cells, drugs, and other molecules for site specific use. For example, since the random coil groups can include charged groups (e.g., repeated segments that include glutamic acid residues), the gels can swell or shrink depending on whether the conditions stabilize or destabilize the charges. In the example in which the segments include many acidic residues, increases in the pH would result in an increased number of deprotonated carboxylic acid residues, thus increasing charge—charge repulsion and causing the gel to swell. Conversely, decreases in pH would protonate the carboxylic acid residues and allow the gel to shrink.

Variables such as peptide sequence, stereochemistry, and length can be precisely controlled by genetic engineering. Each of these variables can affect the temperature, pH, structural packing, and mechanical properties of the gels. Proteins having molecular weights of up to about 190,000 or higher can be made via genetic engineering and can be useful as precursors of monodisperse gels. Non-covalent protein networks can be made wherein the strength of the physical crosslinks, the pore size, and the pH and temperature at which the materials gel are also controlled by varying the amino acid sequence. For example, by matching acidic residues or a helical segment of one copolymer (e.g., in the e & g positions of a heptad repeat unit) with basic residues or helical segment of another copolymer, the physical crosslinks can be made stronger. By shortening the random coil of each copolymer, the pore size can be decreased. The statistical end-to-end distance of a random coil changes with increased molecular weight.

Polymers that Include Non-natural Amino Acids

The incorporation of non-natural amino acids into protein-based materials provides a route for introducing new chemical functionality and physical properties into natural polymer systems. Amino acid analogs can be introduced into cellular proteins either by direct incorporation during protein synthesis or by post-translational modification. There are at least three methods for incorporating non-natural amino acids into proteins: in vivo biological synthesis, in vitro chemical and biological synthesis, and chemical synthesis by solution or solid-phase methods. 5',5',5'-trifluoroleucine (Tfl), for example, can be incorporated into E. coli proteins in the absence of its natural analog, leucine (Leu). Fluorine can mimic the geometry of hydrogen (i.e., the van der Waals radii of fluorine and hydrogen are 1.35 Å and 1.2 Å, respectively), although they differ in chemical character (e.g., the electronegativity of fluorine is 3.98 while that of hydrogen is 2.2). Tfl imparts unique chemical and physiological stability to proteins. For example, the trifluoromethyl group is lipophilic, making it an ideal candidate for the modification of membrane spanning or hydrophobic proteins. Additionally, fluorine-containing amino acids can be studied with nuclear magnetic resonance (i.e., $^{19}$F-NMR) to monitor structural changes in proteins or to determine the motion of fluorinated proteins within lipid bilayers.

The incorporation of Tfl into the helical chain at the d position of the heptad repeat of an α-helical block, which normally encodes leucine during protein synthesis, can be accomplished, for example, using a leucine auxotrophic strain of E. coli. The use of leucine auxotrophs to prepare unique coiled-coil proteins containing Tfl groups can be applied to a variety of proteins where Leu participates in folding, stability, activity, or function. The enhancement of certain physical properties in natural polymer systems can be achieved for biological or materials applications.

Other non-natural amino acids can be incorporated into the copolymers by using the appropriate auxotrophs. For example, selenomethionine, p-fluorophenylalanine, 3-thienylalanine, azetidine-2-carboxylic acid, 3,4-dehydroproline have been incorporated in E. coli. The last two of these non-natural amino acids can be used to add chemical functionality to the copolymers. For example, dehydroproline has a reactive double bond that can be reacted with oxidizing agents, nucleophiles, or reducing agents. Furthermore, deuterated amino acids can be incorporated into the copolymers to afford, for example, sufficient contrast for neutron scattering studies.

Uses of the Gels

The reversible gelling systems can be used, for example, in the molecular recognition of macromolecules, as adhesives (e.g., for bonding glass, metal, or polymers), in thermoreversible and non-covalent fiber networks, and in recyclable materials. The gels can be used as bases for cosmetics, for wound management or wound dressings, or to encapsulate drug molecules for sustained delivery applications.

Because the properties of the gels can be highly sensitive to physical conditions, the gels can find application in gel-based actuators, valves, sensors, motors, switches, artificial muscles, memory devices, optical shutters, filters, toys, paints, coatings, absorbants, bioreactors, micromachines, display devices, and robotics.

The invention will be further described in the following examples, which do not limit the scope of the invention described in the claims.

EXAMPLES

Example 1

Figure 3:
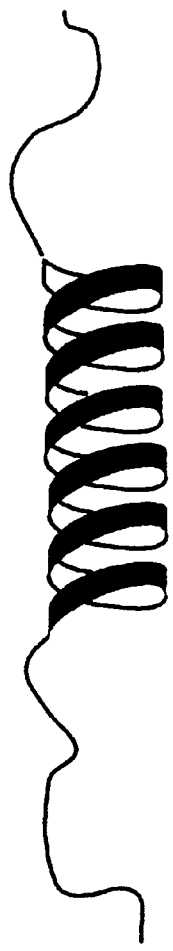
FIG. 3 is a representation of the amino acid sequences for recombinant leucine zipper proteins.
Figure 4A:
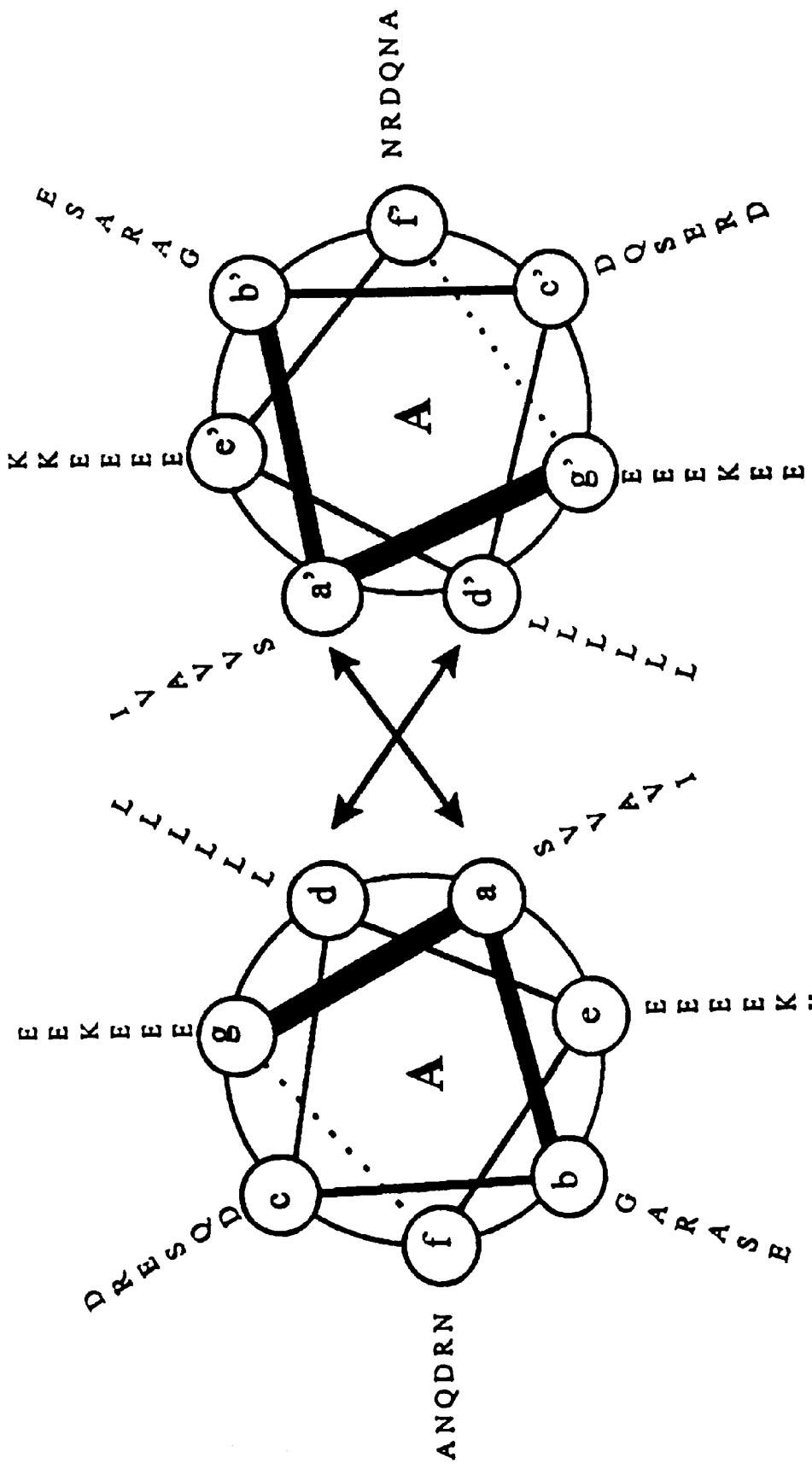
FIGS. 4A, 4B, and 4C are helical wheel representations of parallel coiled-coils of, respectively, a homodimer of an acidic leucine zipper protein called A1, a homodimer of a basic leucine zipper protein called B1, and a heterodimer of A1 and B1.
Figure 4B:
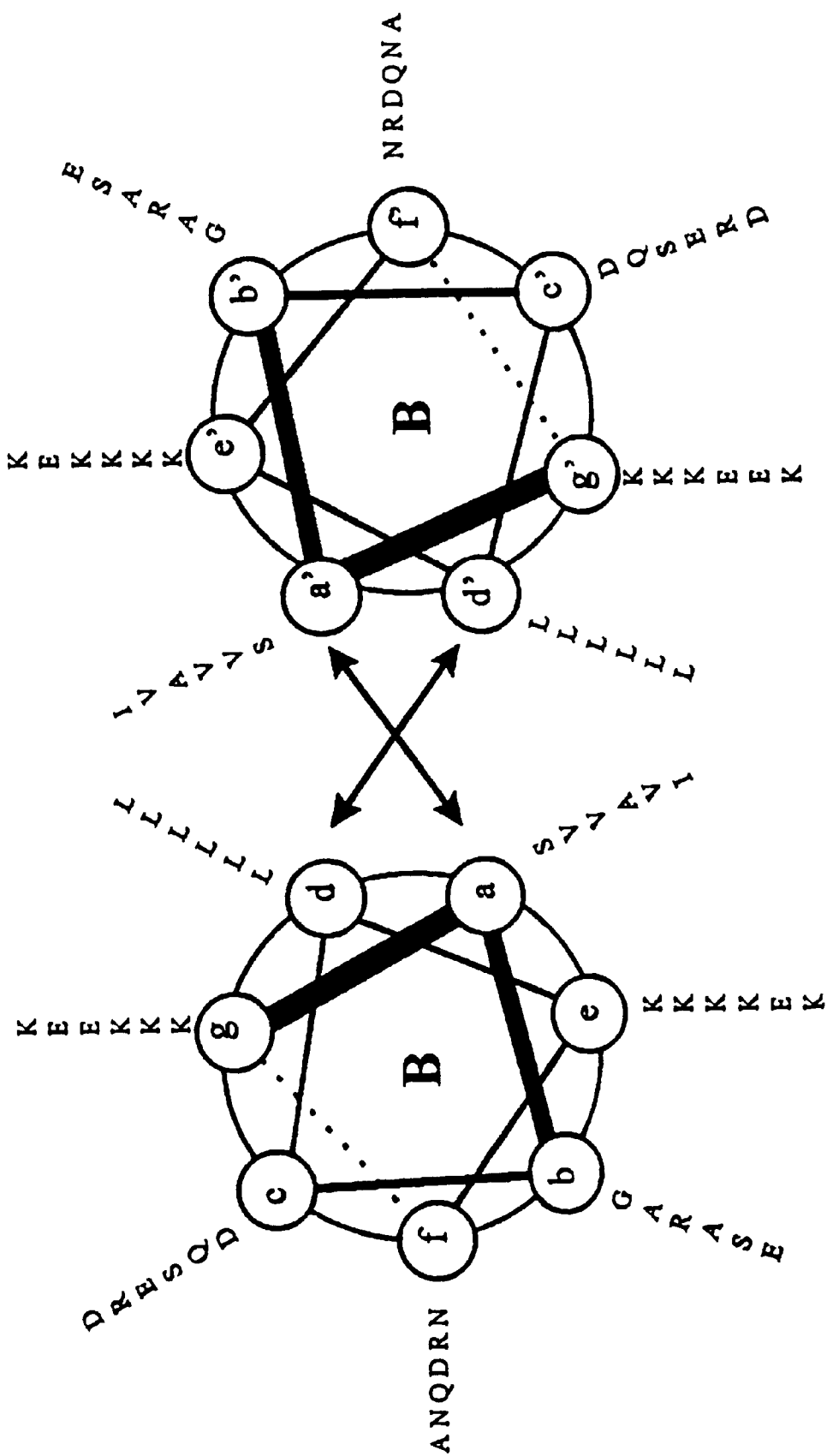
Figure 4C:
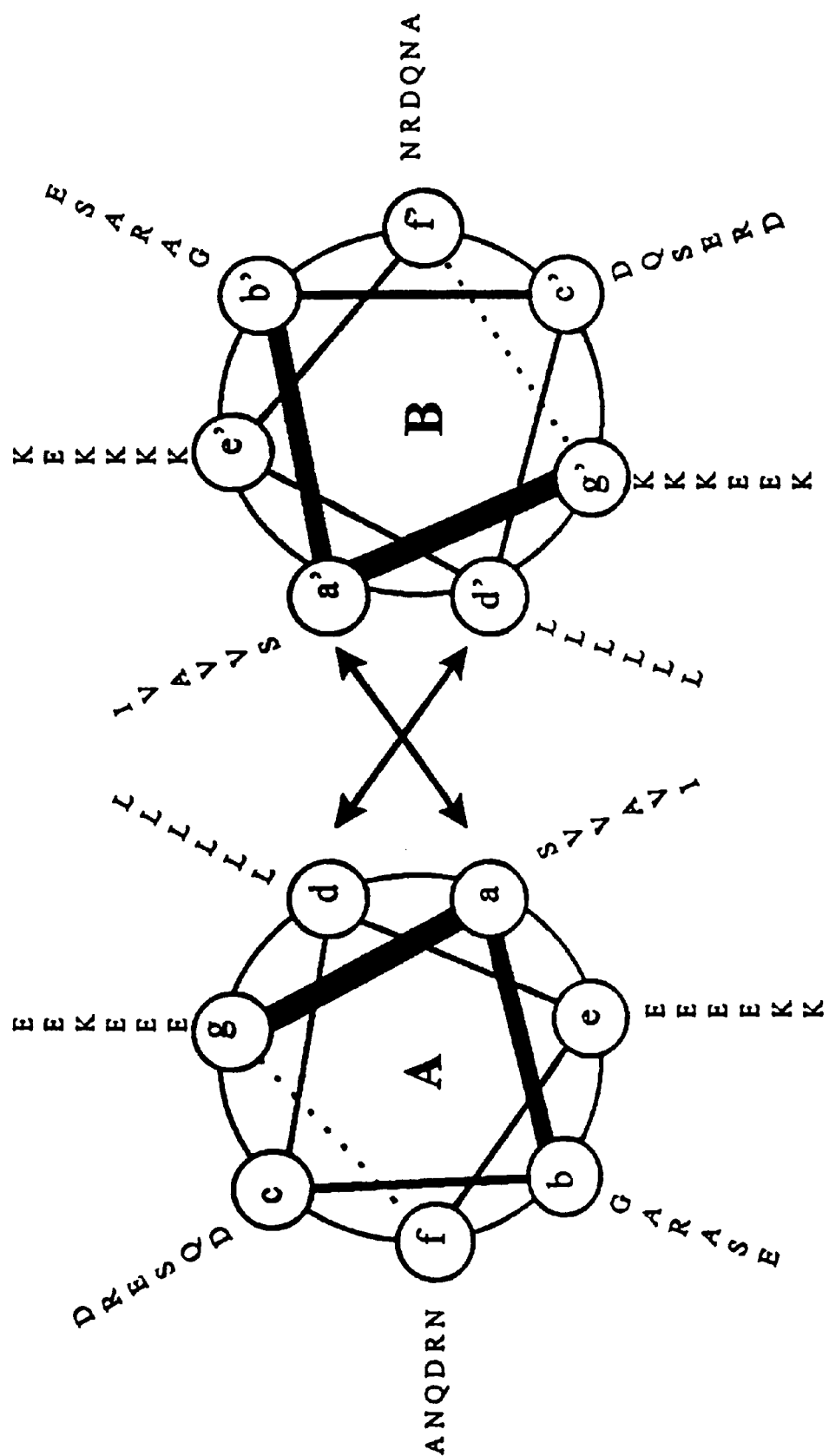
Figure 5A:
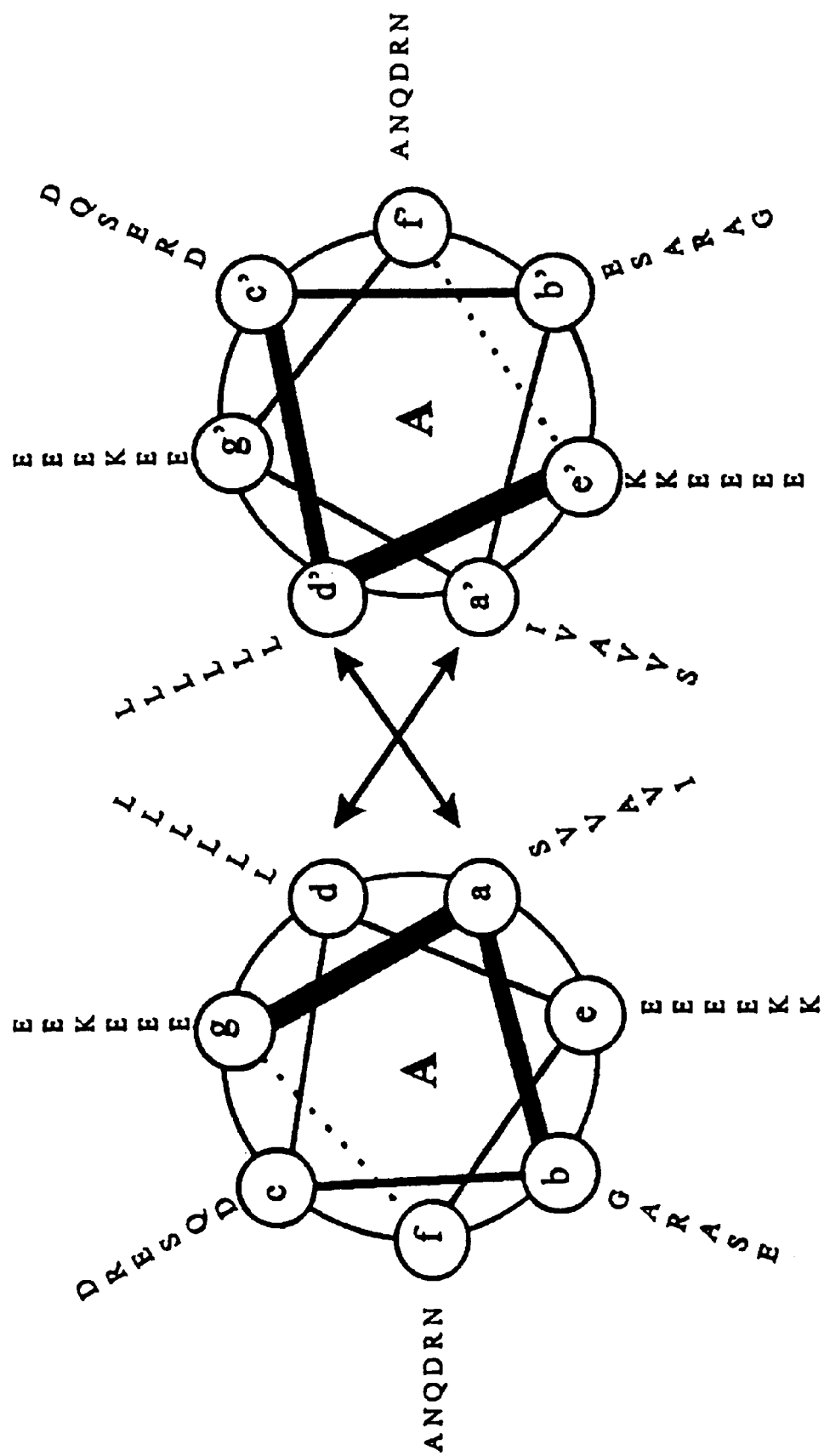
FIGS. 5A, 5B, and 5C are helical wheel representations of antiparallel coiled-coils of A1 homodimer, B1 homodimer, and A1-B1 heterodimer, respectively.
Figure 5B:
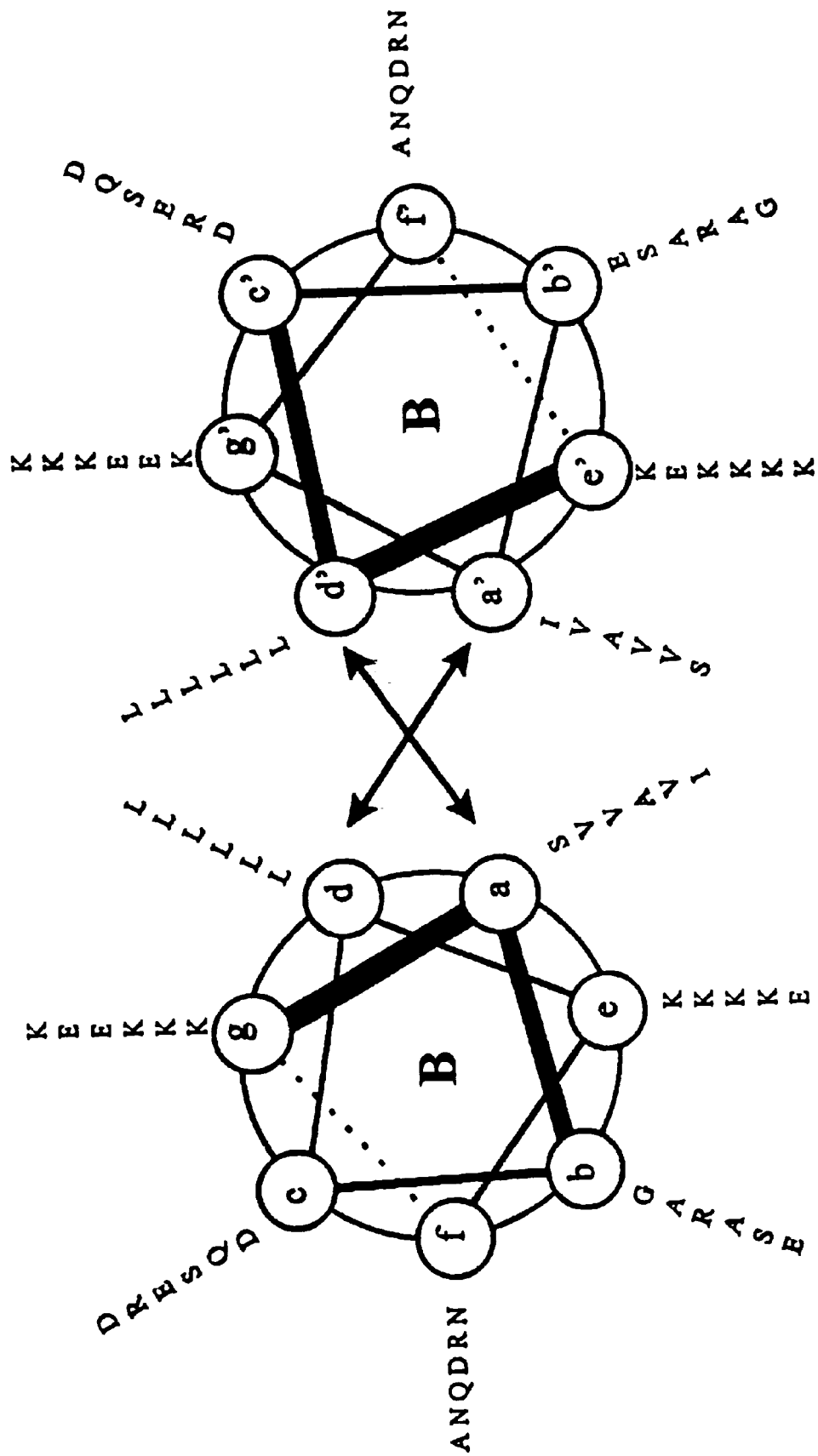
Figure 5C:
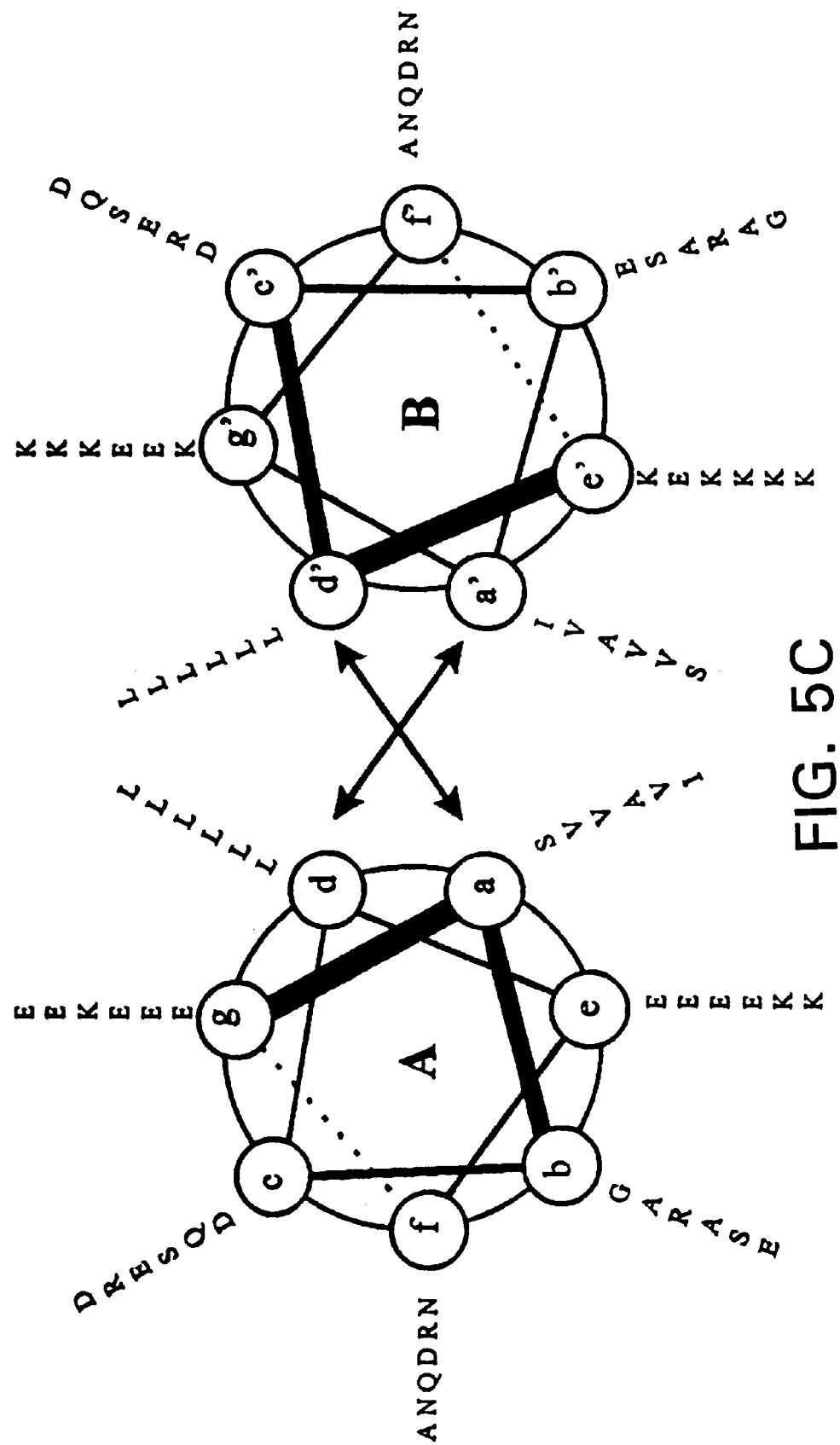

Synthesis of Genetically Engineered Monodisperse Block Copolymers with Helix-Coil-Helix Domains Two similar coiled-coil proteins, A1 and B1, were used as associating α-helical blocks. A schematic drawing of the tertiary structure of these proteins is shown at the top of FIG. 3. Both A1 and B1 proteins contain different 42-amino acid sequences (six internal heptad repeats, a b c d e f g) (SEQ ID NOS: 1 and 2, respectively) which constituted the coiled-coil region of the respective proteins. Each of the 42-amino acid sequences is flanked by the same 14-amino acid N-terminal chain (SEQ ID NO: 3) and 18-amino acid C-terminal chain (SEQ ID NO: 4). Residues that would increase the solubility of the coiled-coil complex in water (e.g., glutamic acid, glutamine, aspartic acid, asparagine, arginine, and serine) were chosen for the b, c, and f positions. Acidic and basic groups, glutamic acid and lysine, respectively, were placed at the e and g positions to provide intermolecular attraction or repulsion between chains. The placement of oppositely charged groups at the e and g positions in the A1 and B1 proteins was designed to maximize heterodimer formation over either homodimer when solutions equimolar in A1 and B1 were mixed. The underlined regions of the A1 and B1 Helix segments in FIG. 3 emphasize this charge pattern at positions e and g. Helical wheels representing parallel and antiparallel arrangements of A1 and B1 homodimers and heterodimers are shown in FIGS. 4 and 5, respectively. The charge pattern at the e and g positions along the heptad repeat distinguishes A1 from B1; the polar charged groups at these positions determine whether the protein chain is predominantly acidic or basic.

The physical properties of the A1 and B1 complexes are listed in Table 1. In the columns labelled "interactions" in the table, A indicates an attractive (i.e., acid-base) interaction and R indicates a repulsive (i.e., acid-acid or base-base) interaction. The calculated interactions include e-g' and e'-g for parallel interhelical dimer interaction, and e'-e and g-g' for antiparallel interhelical dimer interaction. Intrachain interactions include b-f (i to i+4), b-e (i to i+3), c-g (i to i+4), e-b (i to i+4), f-c (i to i+4), f-b (i to i+3) and g-c (i to i+3). Dimer-tetramer dissociation constants were measured by analytical ultracentrifugation for protein solutions (24 to 220 $\mu$M). 95% confidence limits are shown in parentheses.

TABLE 1

| Protein | Charge Pattern at e/g | Parallel Interchain Interactions | Antiparallel Interchain Interactions | Intrachain Interactions | Dimer-Tetramer $K_d$ (in $\mu$M) |
|---|---|---|---|---|---|
| A1 | EEEEEE EKKEKE | 4A 6R | 2A 8R | 12A 16R | 76 (50–112) |
| B1 | KKKKKK KEEEKK | 6A 4R | 4A 6R | 12A 16R | 123 (1–6) |
| A1–B1 | — | 5A 5R | 7A 3R | 12A 16R | — |

Synthesis and Purification of Single-Stranded DNA

Oligonucleotides encoding proteins A1, B1, and random-coil domains were synthesized on a Biosearch Model 8700 DNA synthesizer by phosphoramidite chemistry, and cleaved from polymer supports with 30% ammonium hydroxide at 65° C. The polymer supports were removed by centrifugation and the decanted supernatant was dried in a speed vacuum. The remaining pellets were then resuspended in 1 ml of deionized distilled water (ddH$_2$O) and centrifuged at 15,800 g for 10 minutes at 25° C. to remove any insoluble materials. The remaining aqueous solution of DNA was adjusted to a final concentration of 10 mM magnesium chloride. Absolute ethanol (equilibrated at 25° C.) was added to the DNA solution in a 3:1 ratio.

The mixtures were then cooled at −70° C. for 10 minutes and pelleted at 15,800 g for 10 minutes at 4° C. The supernatant was decanted and the pellet dried in a speed vacuum. The resulting pellets were resuspended in 1 ml of ddH$_2$O and single-stranded DNA was quantitated based on optical absorbance measurements at 260 nm.

Polyacrylamide gel electrophoresis (PAGE; 10% polyacrylamide, 8 M urea) was used to purify the single-stranded DNA. FIGS. 6A and 6B are the sequences of linkers L1 and L2, respectively, showing both the coding (SEQ ID NOS:5,7) and noncoding (SEQ ID NOS: 6,8) strands incorporated in the HindIII and EcoRI restriction sites of cloning vector pUC-18. Important restriction sites are underlined and □ indicates a deletion of a nucleotide. These strands were mixed with 2× formamide loading buffer (containing 0.25% bromophenol blue, 0.25% xylene cyanol FF, and 30% glycerol in water) and heated at 95° C. for 5 minutes before loading onto the preheated gel. The samples were electrophoresed at constant voltage (350 V) for approximately 2 hours. The purified bands corresponding to the purified DNA strands were visualized by ethidium bromide and excised from the gel. Gel slices were crushed in 1 ml of elution buffer (containing 500 mM ammonium acetate; 0.1% sodium dodecyl sulfate, SDS; 10 mM magnesium acetate, and 1 mM ethylenediaminetetraacetic acid dipotassium salt dihydrate, pH 8.0), and incubated overnight at 37° C. on a spin wheel.

Gel residue was removed by centrifugation at 4° C. in filter vials and the supernatants were extracted with 1-butanol to remove ethidium bromide, and then treated with 10 $\mu$l of Type II oyster glycogen (10 $\mu$g/ml), sodium chloride (250 mM), and 0.9 ml absolute ethanol. Mixtures were precipitated at −20° C. overnight, centrifuged at 4° C. for 30 minutes, then decanted. The DNA pellets were washed once with 500 $\mu$l of cold 70% ethanol and redissolved in 50 $\mu$l of ddH$_2$O.

Phosphorylation and Annealing of Single-Stranded DNA

The purified oligonucleotides (L1: coding=5 $\mu$g, noncoding=5 $\mu$g and L2: coding=5 $\mu$g, noncoding=5 $\mu$g) were suspended in about 25 $\mu$l of ddH$_2$O, 5 $\mu$l of 10× T4 polynucleotide kinase buffer (containing 80 mM Tris-HCl pH 7.5, 20 mM dithiothreitol, DTT, 10 mM magnesium chloride, and 1 mM adenosine triphosphate, ATP), 2 $\mu$l of 100 mM ATP, and 1 $\mu$l of T4 polynucleotide kinase (10 Richardson units), to make a final volume of 50 $\mu$l. The reaction tubes were then incubated at 37° C. for 45 minutes and 1 $\mu$l of sodium chloride (5 M) was added to each vial for a final sodium chloride concentration of 100 mM. The mixtures were placed in a 95° C. water bath and equilibrated to room temperature over 10 hours. The annealed duplexes were then extracted with 50:50 phenol:chloroform and washed once with 100% chloroform. 100 $\mu$l of isopropanol and 20 $\mu$l of 3 M sodium acetate were added to each vial and the vials were placed in the −70° C. freezer for 30 minutes. The DNA duplexes were pelleted at 4° C. (15,800 g) for 25 minutes and then dried in the speed vacuum. The pellets were resuspended in 100 $\mu$l of ddH$_2$O.

Ligation of L1 and L2 Duplexes into pUC-18

2.5 $\mu$g of Pharmacia pUC-18 cloning vector was digested with EcoRI (2 units where a unit is the amount of enzyme required to completely digest 1 $\mu$g of substrate DNA in a total reaction volume of 50 $\mu$l) and HindIII (2 units) restriction enzymes. The DNA was visualized on a 1% agarose gel with ethidium bromide and the linearized pUC-18 band was cut and purified with a BIO-RAD™ gel extraction kit. A 33 molar excess of linker to vector (equal volumes) was combined with 2 $\mu$l of 10× ligase buffer (50 mM Tris-HCl, pH 7.8; 10 mM magnesium chloride; 10 mM DTT; 1 mM ATP; and 25 $\mu$g/ml bovine serum albumin, BSA), 0.5 $\mu$l T4 ligase (15 Weiss units), and 7.6 $\mu$l of water to make a total volume of 20 $\mu$l. The resulting ligation mixtures were placed in a 15° C. refrigerator for 21 hours.

Transformation of pUC-18 Containing L1 and L2 into DH5αF' Competent Cells

DH5αF' cells were grown to an optical density at 550 nm (OD$_{550}$) of 0.573, placed on ice for 10 minutes, and collected by centrifugation at 2000 g for 15 minutes at 4° C. The cells were then resuspended in 2 ml of TFB1 Buffer (10 mM morpholinoethanesulfonic acid (MES) pH 6.2; 100 mM rubidium chloride, 10 mM calcium chloride dihydrate, and 50 mM manganese chloride tetrahydrate) by gentle tilting of the tube, adjusted to a final volume of 16 ml. This suspension was left on ice for 15 minutes before the cells were pelleted at 2000 g for 15 minutes and then resuspended in TFB2 buffer (10 mM 3-(N-morpholino)propanesulfonic acid, MOPS; 75 mM calcium chloride dihydrate; 10 mM rubidium chloride; and 15% glycerol). The tube was left on ice for 15 minutes before 200 μl aliquots were dispensed into vials and then stored at −70° C.

Later, competent cells were thawed on ice and 50 μl of the cells were added to 10 μl of the ligation mixtures. The vials were then placed on ice for 2 hours and heat shocked for 3 minutes at 42° C. The vials were then placed on ice for 5 minutes. 500 μl 2xYT medium containing 16 g casein hydrolysate, 10 g yeast extract, and 5 g sodium chloride per liter) was added to the mixtures and incubated for 45 minutes at 37° C. The cells were then spread onto agar plates containing 200 μg/ml ampicillin, and grown for 17 hours.

Figure 7:
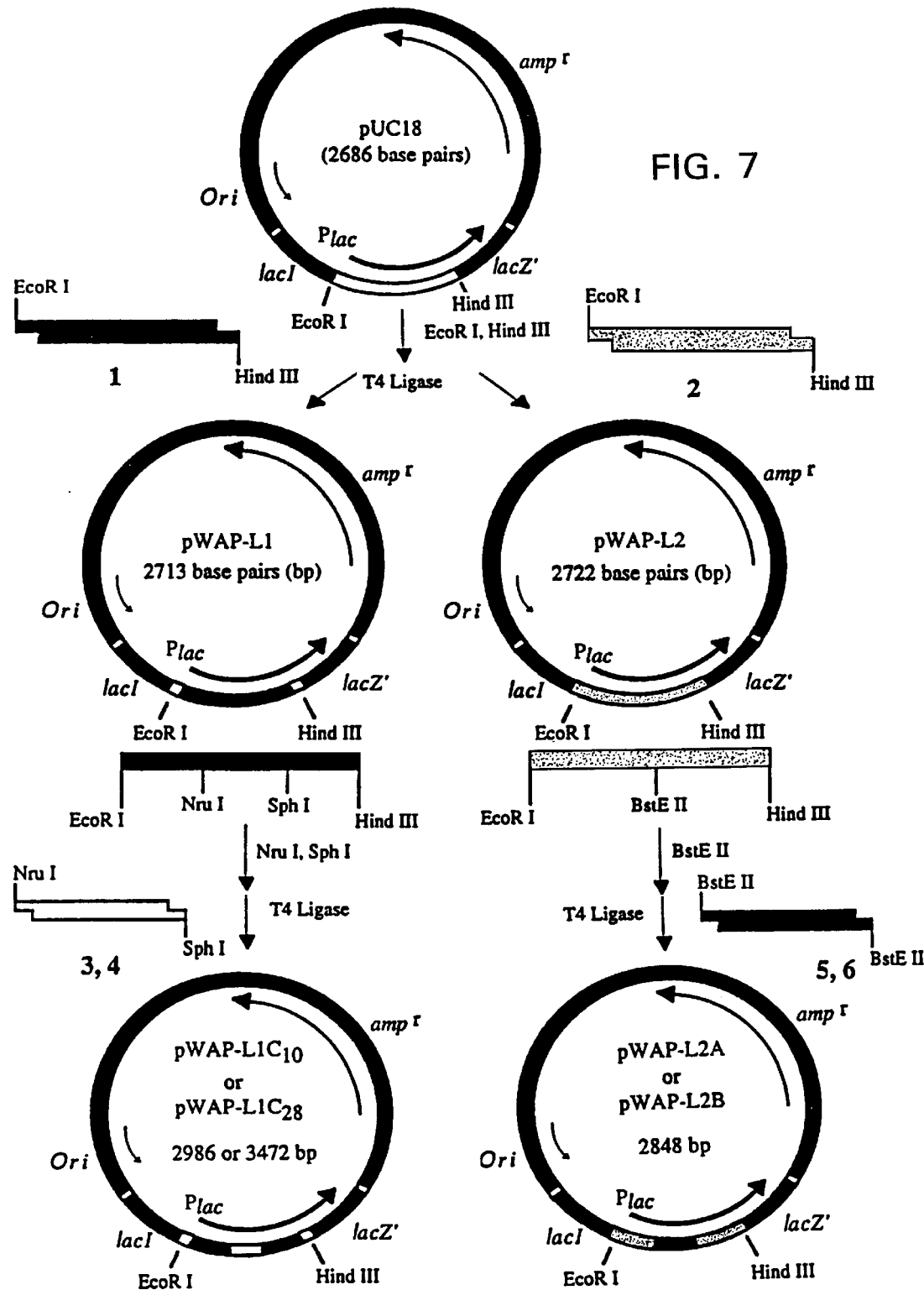
FIG. 7 is a schematic diagram of a strategy for cloning artificial genes encoding random coil and α-helical blocks into pUC18 plasmid DNA.

Mini-preps of pUC-18 Containing L1 and L2 Transformants pUC-18 cloning plasmids containing L1 and L2 DNA were designated as pWAP-L1 and pWAP-L2 respectively (see FIG. 7). Eight colonies of pWAP-L1 and twelve colonies of pWAP-L2 were grown overnight in 2xYT medium containing ampicillin (200 μg/ml).

The DNA from the cell cultures was purified by the following miniprep protocol. A 1.5 ml saturated culture was spun at 13,600 g for 2 minutes and the supernatant was poured off. The cells were resuspended in 200 μl of GTE buffer (containing 50 mM glucose; 25 mM Tris-HCl, pH 8; and 1 mM EDTA, pH 8.0) by repeated pipetting. 200 μl of 3 M sodium acetate (pH 4.8) was added to neutralize the solution, and the mixture was incubated on ice for 5 minutes. The resulting white precipitate was collected by centrifugation at 13,600 g for 5 minutes. The clarified supernatant was transferred to a new 1.5 ml tube containing 2 μl of RNAse A (10 mg/ml) and incubated at 50° C. for 30 minutes. 500 μl of 50:50 phenol:chloroform was added, and the mixture was spun at 13,600 g for 5 minutes. The aqueous layer was decanted and washed once with chloroform. 500 μl of isopropyl alcohol was added. DNA was precipitated for 30 minutes at −20° C. and pelleted at 13,600 g for 30 minutes at 4° C. The supernatant was discarded and the DNA was resuspended into 100 μl of ddH$_2$O before 50 μl of 25% polyethylene glycol (PEG; 8000 molecular weight) in 2.5 M sodium chloride was added. This mixture was incubated for 30 minutes at −20° C., centrifuged at 13,600 g for 30 minutes, and resuspended in 50 μl of ddH$_2$O.

Screening for Inserts L1 and L2 by Enzymatic Digestions

To verify the proper insertion of L1 and L2 DNA into pUC-18, restriction digests of pWAP-L1 and pWAP-L2 were carried out by mixing 15 μl of the plasmid DNA fragments collected in the procedure described above, 5 μl of NEB2 buffer (containing 50 mM sodium chloride, 10 mM Tris-HCl, 10 mM magnesium chloride, and 1 mM DTT, pH 7.9), 1 μl HindIII (20 units), 1 μl NheI (5 units), and 33 μl of ddH$_2$O to give a final volume of 50 μl. The resulting mixtures were then heated for 4 hours at 37° C. The digested DNA was visualized by ethidium bromide on a 1% agarose gel, and colonies confirmed to have the proper inserts were saved for DNA sequencing. In addition to this digestion, individual digestions were carried out for pWAP-L1 and pWAP-L2 as further checks for proper insertion. pWAP-L1 (7 μl) was digested with 0.5 μl of NruI (4 units), 2.5 μl NEBuffer NruI containing 100 mM potassium chloride, 50 mM Tris-HCl, and 10 mM magnesium chloride, pH 7.7), and 15 μl of ddH$_2$O for a final volume of 25 μl. pWAP-L2 was digested with 0.5 μl of XhoI (10 units), 2.5 μl of NEB2 buffer, and 15 μl of ddH$_2$O. The digested DNA was visualized on a 1% agarose gel with ethidium bromide; pUC-18 was used as a positive control since it contains neither NruI nor XhoI restriction sites.

DNA Sequencing of pWAP-L1 and pWAP-L2 Inserted into pUC-18 Cloning Vector

The DNA sequences of pWAP-L1 and pWAP-L2 were confirmed by the Sanger dideoxy sequencing method using the USB SEQUENASE VERSION 2.0.1™ sequencing protocol. Universal (M13/pUC Sequencing Primer (−20) 17mer) and reverse (M13/pUC Sequencing Primer (−47) 24mer) were used to read the coding and anticoding DNA strands, respectively.

Digestion and Removal of Phosphate Groups of pWAP-L1 and pWAP-L2 pWAP-L1 (88 μl, or approximately 220 ng) was first digested with 2.0 μl of NruI (50.8 units) and 10 μl of NruI buffer overnight at 37° C. The DNA was precipitated and isolated, then digested with 1.0 μl of SphI enzyme (5 units), 5 μl of NEB2 buffer, and 44 μl of ddH$_2$O over 5 hours at 37° C. pWAP-L2 (88 μl, or approximately 1 μg) was digested with 2.0 μl BstEII (20 units) and 10 μl NEB3 buffer (containing 100 mM sodium chloride, 50 mM Tris-HCl, 10 mM magnesium chloride, and 1 mM DDT, pH 7.9) at 60° C. overnight. Both pWAP-L1 and pWAP-L2 mixtures were heat inactivated for 20 minutes at 65° C., then 1 μl of calf intestinal alkaline phosphatase (CIP; 10 units) was added to the pWAP-L1 digestion mixture, and 8 μl of CIP (80 units) was added to the pWAP-L2 digestion mixture. EDTA was added to each solution to give a final concentration of 5 mM, and the reaction mixtures were heated to 65° C. for 1 hour. The DNA was extracted with phenol and precipitated with 20 μl of sodium acetate and 120 μl of 100% ethanol. The precipitated DNA was resuspended in 40 μl of TE buffer (10 mM Tris-HCl and 1 mM EDTA, pH 8.0) before being run on a 1% agarose gel. Gel slices were excised, and the DNA was extracted and purified by Bio-Rad DNA purification method.

Insertion and Verification of Random-Coil and Helical DNA Sequences into Linearized pWAP-L1 and pWAP-L2

DNA fragments encoding [(AG)$_3$PEG]$_{10}$ (FIG. 8; SEQ ID NOS:9,10) and [(AG)$_3$PEG]$_{28}$ (FIG. 9; SEQ ID NOS: 11,12) were ligated into linearized pWAP-L1 at SphI/NruI. The SphI/NruI sites in the DNA fragments were derived from a fragment obtained from Protein Polymer Technologies, Inc (San Diego, Calif.). In addition, DNA fragments encoding α-helical acidic leucine zipper (FIG. 10A; SEQ ID NOS: 13,14) and basic leucine zipper (FIG. 10B; SEQ ID NOS: 15,16) sequences were ligated into linearized pWAP-L2 at the BstEII site. The restriction sites are underlined in FIGS. 8, 9, 10A, and 10B. Prior to ligation, the DNA fragments encoding [(AG)$_3$PEG]$_{10}$ and [(AG)$_3$PEG]$_{28}$ were obtained from pET3-5 and pET3-14 plasmids, respectively, by cutting with SphI and NruI. Likewise, the DNA molecules encoding the acidic and basic leucine zippers were digested from pUC-LINKA1 with BstEII enzyme. Purified pieces were ligated into the linear pWAP-L1 or pWAP-L2 by combining 10 μl of insert, 10 μl of vector, 2.5 μl of ligase buffer, 0.5 μl of T4 DNA ligase, and 2.0 μl of ddH$_2$O.

The ligation mixtures were then used to transform DH5αF' cells and the resultant transformants were screened for proper DNA insertion by enzymatic digestions. Plasmids containing the DNA encoding [(AG)$_3$PEG]$_{10}$ and [(AG)$_3$PEG]$_{28}$ were digested with NdeI and SphI, whereas plasmids containing the DNA encoding the acidic and basic leucine zippers were digested with NdeI and BglII. The sequences of all of the combined DNA molecules were confirmed by the Sanger dideoxy sequencing method mentioned previously. Plasmids were designated pWAP-L1C$_{10}$, pWAP-L1C$_{28}$, pWAP-L2A, and pWAP-L2B as shown in FIG. 7. One difference between the L1 and L2 designation is that L1 codes for a single tryptophan at the C-terminus whereas L2 codes for a single cysteine at this end. A and B are acidic and basic leucine zipper proteins, respectively, and C$_n$ is the random-coil [(AG)$_3$PEG]$_n$(SEQ ID NO: 23) repeat. The sequences of L2-A, L2-B, and L1-C$_{10}$ are shown in Table 2, in which the A, B, and C$_{10}$ sequences are printed in bold-face type.

pWAP-L1AC$_{10}$B, pWAP-L1BC$_{10}$B, pWAP-L2AC$_{10}$A, pWAP-L2AC$_{10}$B, pWAP-L2BC$_{10}$B, pWAP-L2AC$_{28}$A, pWAP-L2AC$_{28}$B, and pWAP-L2BC$_{28}$B, respectively.

BamHI Digestions of DNA Molecules pWAP-L2A, pWAP-L2B, pWAP-L1C$_{10}$, pWAP-L1AC$_{10}$A, pWAP-L1AC$_{10}$B, pWAP-L1BC$_{10}$B, pWAP-L2AC$_{10}$A, pWAP-L2AC$_{10}$B, pWAP-L2BC$_{10}$B, pWAP-L2AC$_{28}$A, pWAP-L2AC$_{28}$B, and pWAP-L2BC$_{28}$B DNA were grown in DH5αF' host cells in 100 ml 2xYT medium with ampicillin (200 μg/ml) and isolated using Qiagen maxiprep DNA columns. 43 μl (approximately 300 ng) of each plasmid was combined with 5 μl of NEB BamHI buffer containing 150 mM sodium chloride, 10 mM magnesium chloride, 1 mM DDT, pH 7.9 and 2 μl of BamHI (40 units) and incubated overnight at 37° C. (FIGS. 13 and 14) Qiagen pQE9 expression vector (Chatsworth, Calif.) DNA was also cut with BamHI and dephosphorylated by the CIP protocol

TABLE 2

L2-A:
MRGSHHHHHHGSDDDDKWASGDLENEVAQLEREVRSLEDEAAELEQKVSRLKNEIEDLKA (SEQ ID NO:17)
EIGDHVAPRDTSMGGC

L2-B:
MRGSHHHHHHGSDDDDKWASGDLKNKVAQLKRKVRSLKDKAAELKQEVSRLKNEIEDLKA (SEQ ID NO:18)
KIGDHVAPRDTSMGGC

L1-C$_{10}$:
MRGSHHHHHHGSDDDDKASYRDPMGAGAGAGPEGAGAGAGPEGAGAGAGPEGAGAGAGPE (SEQ ID NO:19)
GAGAGAGPEGAGAGAGPEGAGAGAGPEGAGAGAGPEGAGAGAGPEGARMPT
SW

Enzymatic Digestions of DNA at NheI and SpeI Restriction Sites

To recombine the DNA described above to form DNA that encodes the triblocks A-C$_n$-A, A-C$_n$-B, and B-C$_n$-B, a series of digestions and ligations were carried out at the NheI and SpeI enzymatic restriction sites. FIGS. 11 and 12 represent two different routes to prepare the coding sequences of the triblock copolymers. The combination of DNA was achieved through NheI and SpeI sites located outside of the helix and coil regions of the DNA. NheI and SpeI sites are compatible; upon ligation of a NheI to a SpeI end, or vice versa, the site is destroyed. Both restriction sites have the same middle four nucleotide bases that allow them to combine upon ligation, as shown below:

| NheI | 5' | G | C | T | A | G | C | 3' |
|---|---|---|---|---|---|---|---|---|
|  | 3' | C | G | A | T | C | G | 5' |
| SpeI | 5' | A | C | T | A | G | T | 3' |
|  | 3' | T | G | A | T | C | A | 5' |

The frequency at which NheI cut ends combine with SpeI cut ends is approximately 50%. In all cases, NheI and SpeI digestions were carried out in a total volume of 25 μl; enzymatic buffer, enzyme, ddH$_2$O, and DNA volumes were adjusted accordingly. Miniprep, transformation, and phosphate removal procedures were carried out as described above. 2% Agarose gels were used in the verification, quantification, and isolation of the various DNA.

DNA encoding twelve different proteins (i.e., A-Cys, B-Cys, C$_{10}$-Trp, AC$_{10}$A-Trp, AC$_{10}$B-Trp, BC$_{10}$B-Trp, AC$_{10}$A-Cys, AC$_{10}$B-Cys, BC$_{10}$-Cys, AC$_{28}$A-Cys, AC$_{28}$B-Cys, and BC$_{28}$B-Cys) was made through the series of steps described above. The DNA molecules were designated pWAP-L2A, pWAP-L2B, pWAP-L1C$_{10}$, pWAP-L1AC$_{10}$A, as previously described (FIGS. 13 and 14). The fragments were visualized on 2% agarose gels and excised for purification by BIO-RAD™ DNA binding beads. Quantification of the recovered DNA was made on 2% agarose gels.

Ligation of DNA Molecules

A 5 molar excess of linker to vector was combined with 2.5 μl ligation buffer, 0.5 μl ligase, and ddH$_2$O for a total volume of 25 μl. The ligated mixtures were transformed into K-12 E. coli strain SG13009 (Qiagen, Chatsworth, Calif.) containing repressor plasmid, pREP4 (Qiagen, Chatsworth, Calif.). Mixtures were spread onto 2xYT agar plates containing 200 μg/ml ampicillin and 50 μg/ml kanamycin, and incubated for 16 hours at 37° C. Single colonies were grown to saturation in 5 ml of 2xYT medium and the DNA was isolated. Restriction digests were used to verify orientation, size, and digest sites of the DNA from the transformed colonies. These were accomplished with NheI, EcoRI/HindIII, and BamHI restriction enzymes, respectively. Colonies containing the correct inserts were then used in the following bacterial expression procedures.

Protein Expression in pQE9-derived Expression Vectors

Recombinant vectors (pQE9) containing the targeted sequences were used for protein expression in host cells of strain SG13009 containing repressor plasmid (pREP4) (FIGS. 13 and 14). New plasmid designations are pQE9-L2A, pQE9-L2B, pQE9-L1C$_{10}$, pQE9-L1AC$_{10}$A, pQE9-L1AC$_{10}$B, pQE9-L1BC$_{10}$B, pQE9-L2AC$_{10}$A, pQE9-L2AC$_{10}$B, pQE9-L2BC$_{10}$B, pQE9-L2AC$_{28}$A, pQE9-L2AC$_{28}$B, and pQE9-L2BC$_{28}$B. Saturated cultures containing the targeted DNA sequences were grown in 25 ml of 2xYT medium with ampicillin (200 μg/ml) and kanamycin (50 μg/ml) for 15 hours at 37° C. These cultures were then transferred to 2 l flasks, each containing 1 l sterilized 2xYT medium (with ampicillin and kanamycin). The cultures were incubated for an additional 6 hours at 37° C. with vigorous aeration until the optical densities at 600 nm (OD$_{600}$) were in excess of 2.1 mM. Isopropyl-β-thiogalactoside (IPTG) was added and protein synthesis was induced for a period of 4 hours at 37° C. The cells were then centrifuged (22,100 g for 30 minutes), the supernatant was removed, and 50 ml of 6 M guanidine-HCl buffer containing dibasic sodium phosphate (0.1 M, pH 8) was added. The cells were lysed by storing in a −80° C. freezer, then the supernatant was collected for protein purification by centrifugation at 22,100 g for 50 minutes. The clarified supernatant was loaded onto a nickel-NTA affinity column at pH 8 and the bound target proteins were washed with 8 M urea buffers at pH 8, 7, and 6, then eluted at pH 5. The appropriate fractions were dialyzed against deionized water, then they were freeze-dried. The final weights of the purified target proteins were in the range of 20–160 mg per 1 l of cell growth medium, after purification with Ni$^{2+}$ metal affinity chromatography.

Matrix Assisted Laser Desorption Mass Spectrometry (MALDI-MS) with Time-of-Flight Analyzer (TOF)

MALDI-TOF mass spectrometry of the gas-phase protein ions was performed on a LASERMAT 2000™ (Finnigan Mat, San Jose, Calif.) by the Analytical Chemistry and Peptide/DNA Synthesis Facility at Cornell University, Ithaca, N.Y. The protein samples were mixed with a molar excess of matrix solution (0.05 M 3,5-dimethoxy-4-hydroxycinnamic acid for predicted masses greater than 20,000 and 0.05 M α-cyano-4-hydroxycinnamic acid for predicted masses less than 20,000 in 30% acetonitrile/water, 0.1% trifluoroacetic acid) before approximately 0.5 μl was dried onto the sample probe. The surface of the probe was irradiated with a nitrogen laser at 337 nm. Detection of the protein ions were recorded in the positive ion mode with laser power ranging between 10–25 kV. The results of the MALDI experiments are summarized in Table 3. The weights are average molecular weights and refer to the protonated form of the polypeptides.

TABLE 3

| Domain Structure | [M + H] + (calculated) | [M + H] + (observed) | Relative Error (%) |
| --- | --- | --- | --- |
| A-Cys | 8550 | 8548 | 0.02 |
| B-Cys | 8545 | 8559 | 0.16 |
| C-Trp | 10384 | 10433 | 0.47 |
| AC$_{10}$A-Trp | 22092 | 22317 | 1.02 |
| AC$_{10}$B-Trp | 22086 | 22133 | 0.21 |
| BC$_{10}$B-Trp | 22080 | 22165 | 0.38 |
| AC$_{10}$A-Cys | 22440 | 22478 | 0.17 |
| AC$_{10}$B-Cys | 22434 | 22506 | 0.32 |
| BC$_{10}$B-Cys | 22429 | 22402 | 0.12 |
| AC$_{28}$A-Cys | 34451 | 33148 | 3.78 |
| AC$_{28}$B-Cys | 34446 | 34567 | 0.35 |
| BC$_{28}$B-Cys | 34440 | 35712 | 3.69 |

Quantitative Amino Acid Compositional Analysis

Amino acid analysis was performed by the Analytical Chemistry and Peptide/DNA Synthesis Facility at Cornell University, Ithaca, N.Y. Amino acid analysis was carried out on a PICO-TAG™ Amino Acid Analysis System (Millipore Corp., Bedford, Mass.). Duplicate samples were hydrolyzed in constant boiling hydrochloric acid for 110 minutes at 150° C. Appropriate blanks, controls and standards were hydrolyzed in the same vessel as the batch hydrolysis. The amino acids were derivatized with phenyl isothiocyanate (PITC) and analyzed by reversed phase HPLC. The resulting phenylthiocarbamoyl amino acid derivatives were separated on a 4.6×300 mm NOVA PACK™ C18 column employing a modified Pico-Tag buffer system and detected at 254 nm.

The purified proteins were resolved on a polyacrylamide minigel and visualized by staining with Coomassie Brilliant Blue R-250. The results of the analysis were all consistent with the desired sequences, within the error range of the instrumentation.

Thermodynamic Analysis

Figure 15:
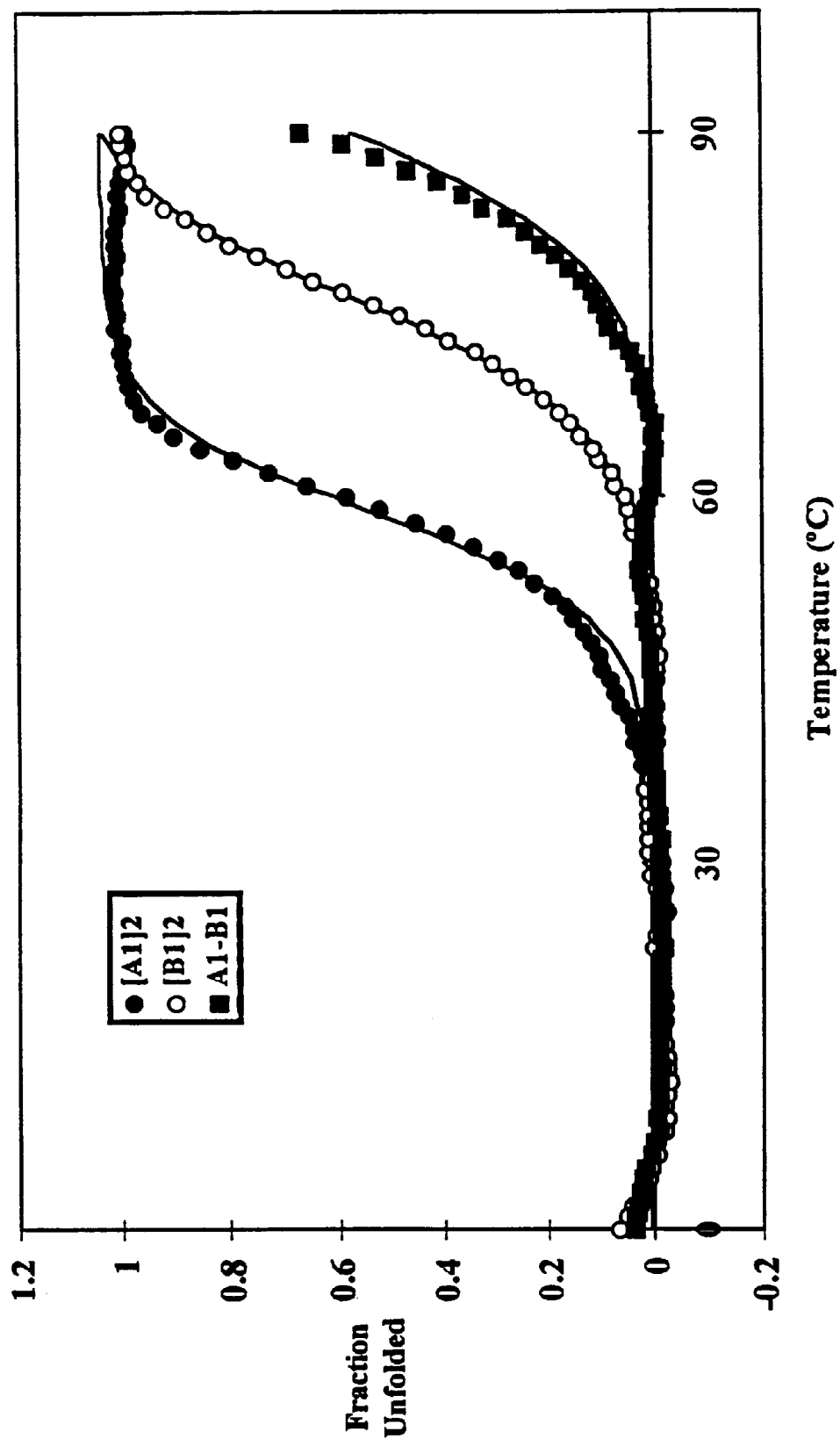
FIG. 15 is a plot of the thermal melting profiles of the A1-A1 (●), B1-B1 (○), and A1-B1 (■) dimers.
Figure 16:
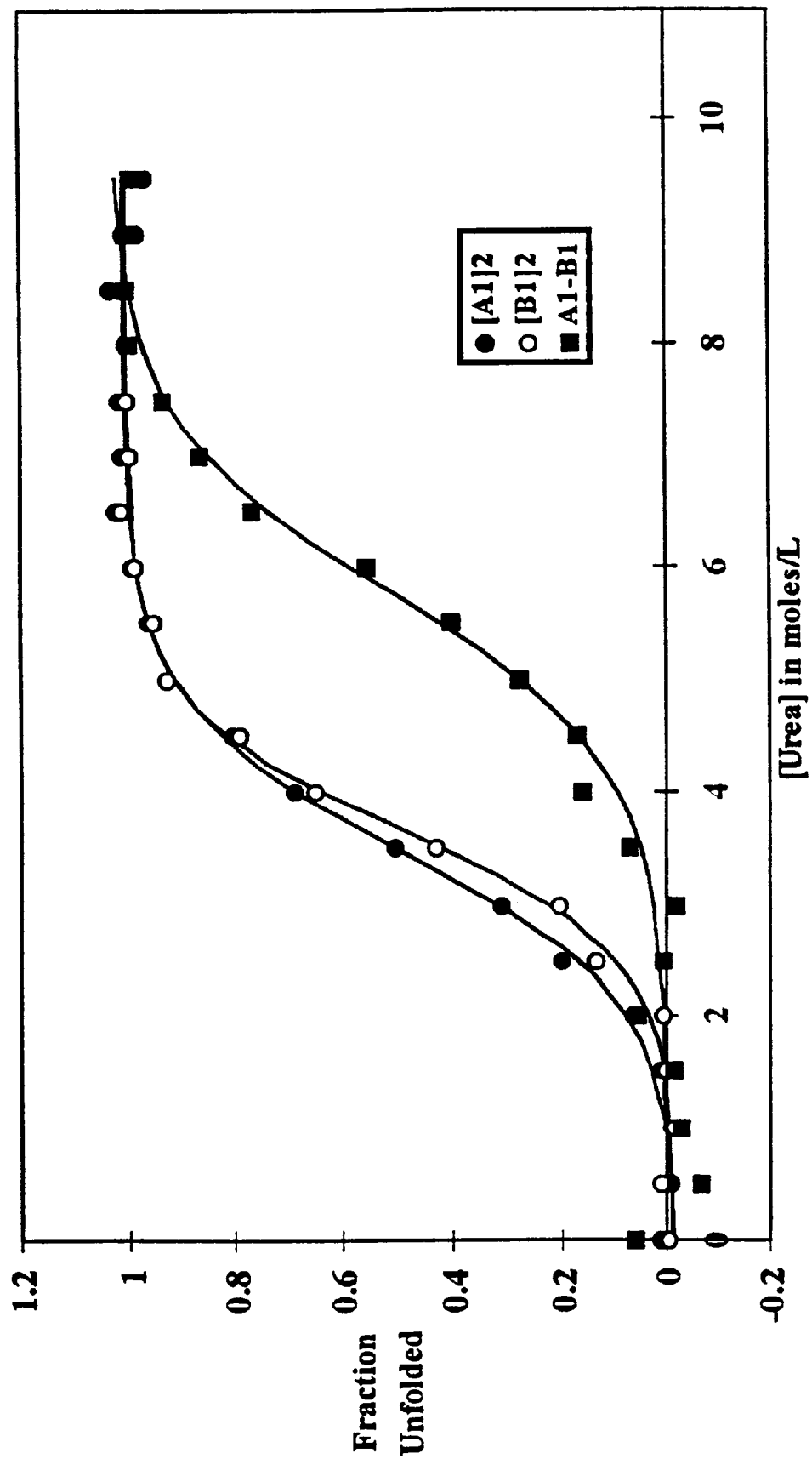
FIG. 16 is a plot of urea denaturation profiles of the A1-A1 (●), B1-B1 (○), and A1-B1 (■) dimers.

Thermal and urea denaturation studies were done with 3 μM solutions of A1, B1, and A1-B1 complexes and the results are shown in FIGS. 15 (thermal) and 16 (urea denaturation). The fraction of unfolded peptide in FIG. 15 was determined by monitoring CD spectra at 222 nm (3 μM protein in 50 mM monobasic sodium phosphate, 100 mM sodium chloride, pH 7.4). The graph in FIG. 15 suggests that the folded-to-unfolded transition temperature for equimolar mixtures of A1 and B1 is higher than that of either A1-A1 or B1-B1 solutions. This implies that the A1-B1 coiled-coils are more stable than A1-A1 or B1-B1 coiled coils. The fraction of unfolded peptide in FIG. 16 was determined by monitoring CD spectra at 222 nm as a function of urea concentration over the range of 0 to 9.5 M, with 3 mM protein concentration in 50 mM monobasic sodium phosphate and 100 mM sodium chloride, pH 7.4.

The temperature curves showed that the thermal transition temperature, T$_m$, from a folded to an unfolded state was higher for the A1-B1 mixture than either of the A1-A1 or B1-B1 solutions. These results were consistent with urea denaturation profiles that show a higher [urea]$_{1/2}$ (transition where 50% of the helix is unfolded at 20° C.) for the unfolding process of A1-B1 than for the A1-A1 and B1-B1. Thus, at pH 7.4 the heterodimer complexes were more stable than either of the homodimer complexes.

Table 4 compares the data collected and calculated from these curves for A1-A1, B1-B1, and A1-B1 interactions. In Table 4, T$_M$ is the temperature at which 50% of the helix is unfolded in 50 mm sodium phosphate, 100 mm sodium chloride, ph 7.4; [urea]$_{1/2}$ is the concentration of urea at which 50% of the helix is unfolded at 20° C.; and ΔG$_u$ is the molar free energy of folding calculated from the urea denaturation profiles. These data showed that the transition temperature for the heterodimer complex was higher than that of either homodimer solution.

TABLE 4

| Dimer Complex | T$_m$ in PBS (° C.) | [Urea]$_½$ (M) | slope m | ΔG$_u$ (Kcal/mole) | ΔΔG$_u$ (Kcal/mole) |
| --- | --- | --- | --- | --- | --- |
| A1—A1 | 58.3 | 3.57 | −1.295 | 11.54 | 0.00 |
| B1—B1 | 75.5 | 3.66 | −1.512 | 12.55 | 0.13 |
| A1-B1 | 86.3 | 5.76 | −1.165 | 13.76 | 2.75 |

A two state mechanism was used to describe the equilibrium between folded and unfolded protein states. Table 4 indicates that the free energy of unfolding, ΔG$_u$, and the difference in the free energies of unfolding, ΔΔG$_u$, also increase upon mixing of equimolar solutions of A1 and B1. ΔG$_u$ is obtained by plotting lnK$_{d,u}$ (i.e., the equilibrium constant for dissociation of the dimers) against the concentration of denaturant, then extrapolating back to zero denaturant concentration. ΔΔG$_u$ is determined by comparing the free energy values of proteins that are calculated when 50% of the protein has unfolded in the presence of a denaturant. The latter method minimizes any errors introduced in the measurement of the slope by extrapolation to zero.

Figure 17:
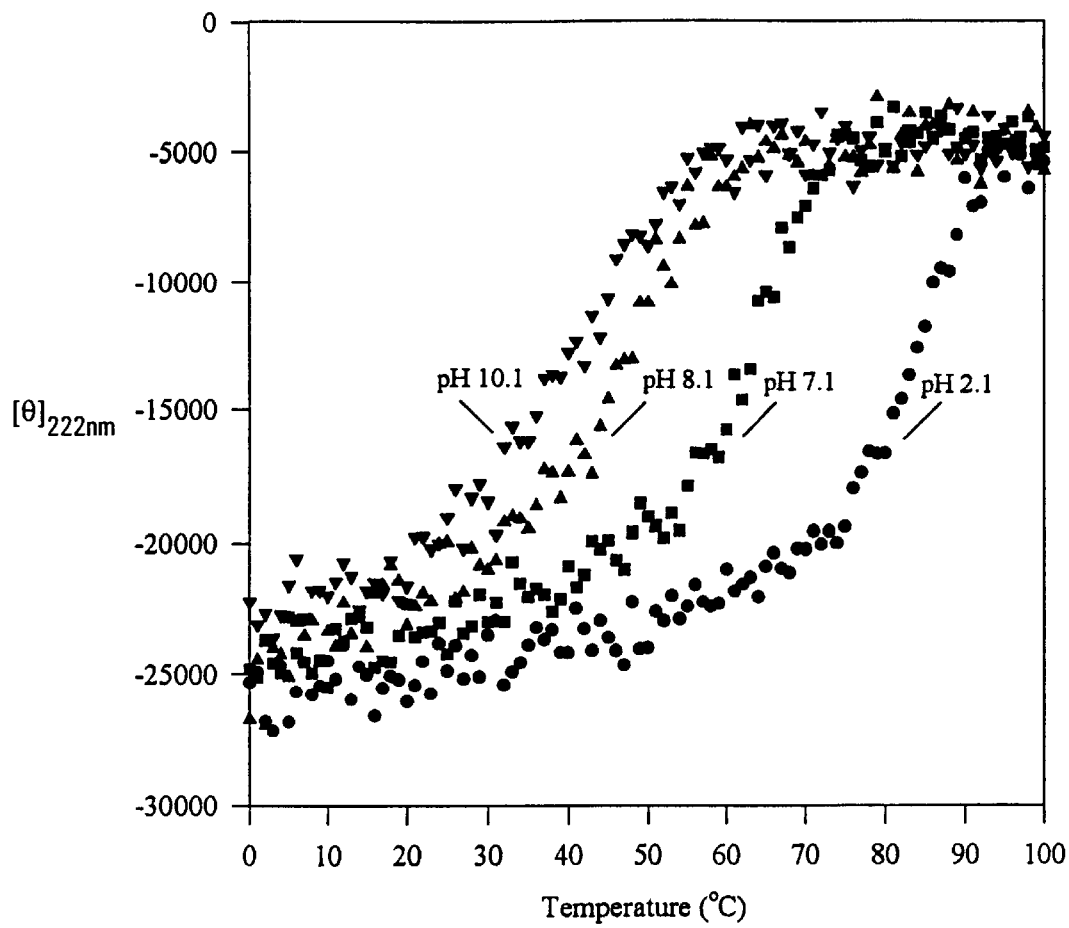
FIG. 17 is a graph of thermal denaturation curves recorded at 222 nm for A1 homodimer at various pHs.
Figure 18:
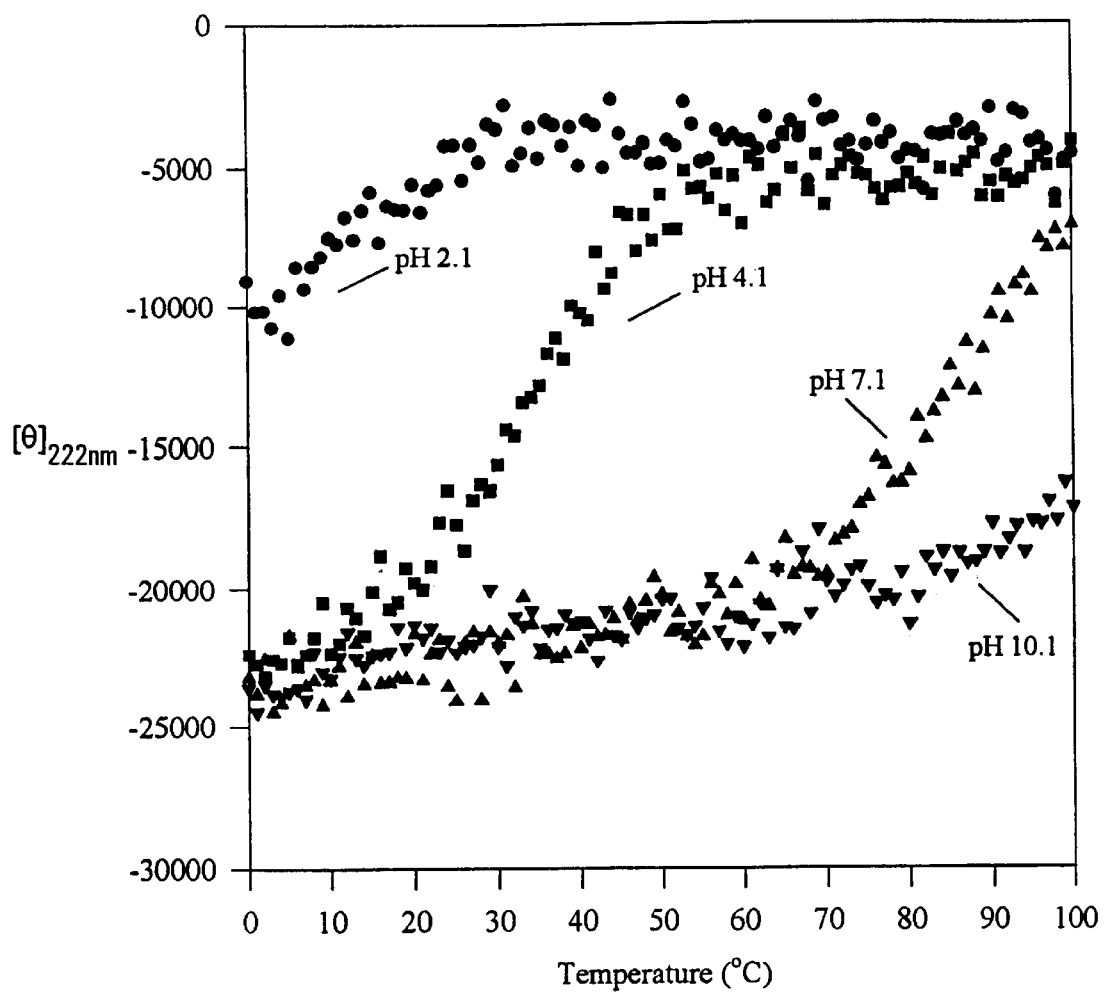
FIG. 18 is a graph of thermal denaturation curves recorded at 222 nm for B1 homodimer at various pHs.
Figure 19:
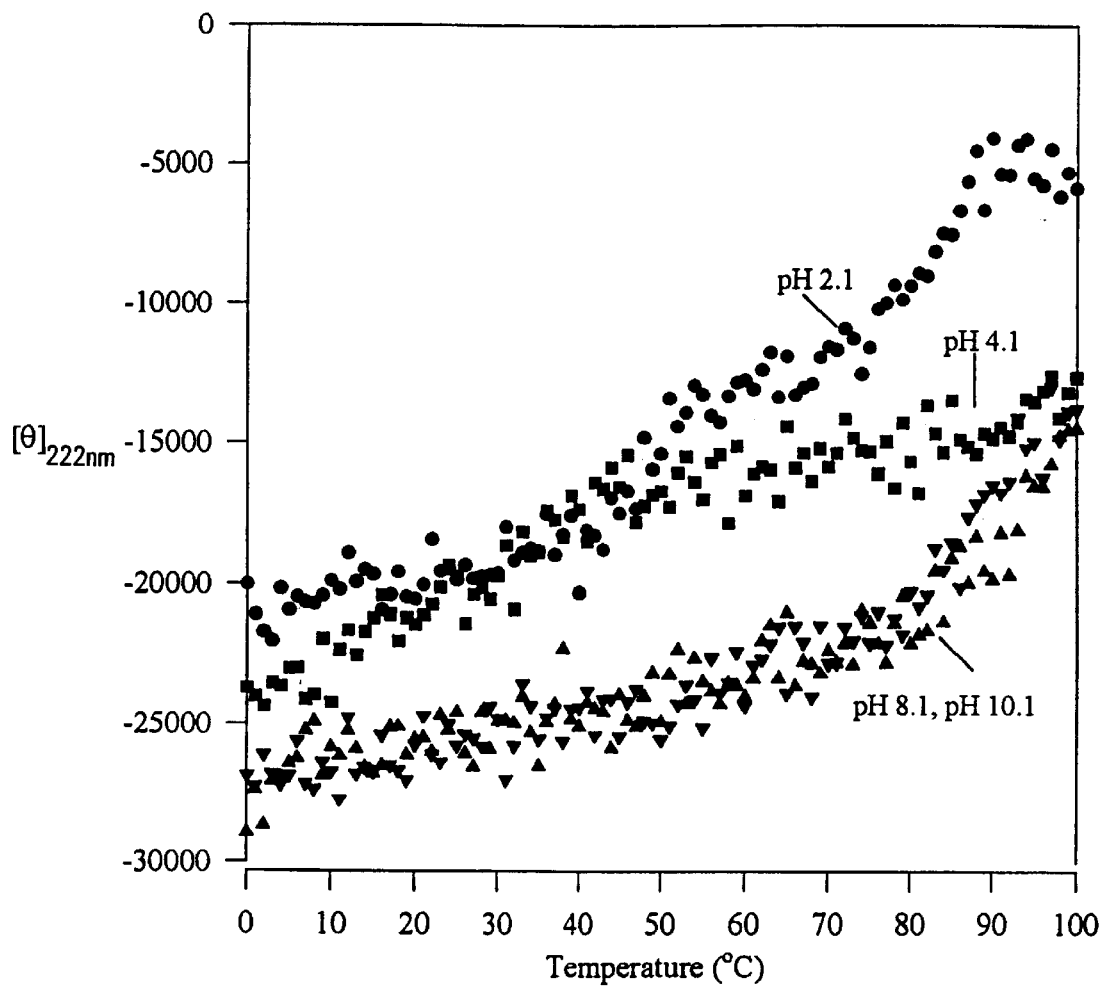
FIG. 19 is a graph of thermal denaturation curves recorded at 222 nm for A1-B1 heterodimer at various pHs.

Thermal denaturation curves as a function of pH were recorded at 222 nm with 12 μM solutions of A1, B1, and the A1-B1 mixture (in 10 mM monobasic sodium phosphate at pH 2.1, 7.1, 8.1, and 10.1) and are shown in FIGS. 17, 18, and 19, respectively. At lower pH values, the thermal transition occurred at higher temperatures for A1. It can be theorized that this is because the A1 chains contain carboxylic acid groups at the e and g positions in the heptad repeat and lower pH values can therefore promote the formation of coiled coils as the sidechains remain protonated. At higher pH values, the negatively charged carboxylate groups can cause interchain electrostatic repulsion and reduce the stability of the coiled coil structure. The opposite trend was observed for B1, consistent with the argument above; the B1 chains have basic lysine sidechains at the e and g positions. The data for the equimolar mixture of A1 and B1 showed that at every pH the transition shifted to a higher temperature.

Example 2
Reversible Hydrogels from Self-Assembling Artificial Proteins

Oligonucleotides were synthesized on a BIOSEARCH™ Model 8700 DNA synthesizer and ligated into the polylinker region of the pUC18 cloning vector. A 213 bp fragment encoding α-helical protein A-Cys was ligated into the EcoRI and HindIII restriction sites of pUC18 to yield pWAP-L2A. Likewise, a 351 bp fragment encoding random-coil protein $C_{10}$-Trp was ligated into the EcoRI and HindIII restriction sites of pUC18 to yield pWAP-L1C. Recombinant DNA was cloned in *E. Coli* strain DH5αF' before coding and noncoding sequences were verified by DNA sequence analysis. DNA fragments that encode A-Cys and $C_{10}$-Trp independently were used to form recombinant DNA that encodes $AC_{10}$A-Cys. This combination of DNA was achieved through NheI and SpeI sites. All DNA fragments were isolated by BamHI digestion, and directionally ligated into the *E. coli* expression vector pQE9 (Qiagen, Chatsworth, Calif.) to form an $NH_2$-terminal His fusion product. Recombinant DNA plasmids encoding A-Cys, $C_{10}$-Trp, and $AC_{10}$A-Cys were designated pQE9-L2A, pQE9-L1$C_{10}$, and pQE9-L2$AC_{10}$A, respectively. The host used for protein expression was *E. coli* strain SG13009, containing the pREP4 repressor plasmid (Qiagen, Chatsworth, Calif.). Cultures containing these DNA sequences were grown at 37° C. in 2 l of TB medium (containing 16 g Bacto-Tryptone, 10 g yeast extract, and 5 g sodium chloride per liter) with ampicillin (100 μg/ml) and kanamycin (50 μg/ml) until the optical densities at 600 nm ($OD_{600}$) were in excess of two. 1 mM of isopropyl-β-thiogalactoside (IPTG) was added and protein synthesis was induced for a period of 4 hours at 37° C. The cells were then centrifuged at 22,100 g for 30 minutes, and 50 ml 6 M guanidine-HCl buffer containing dibasic sodium phosphate (0.1 M, pH 8) was added. The cells were lysed by storing in a −80° C. freezer and the supernatant was collected for protein purification. Metal affinity chromatography was used to purify the target proteins, using nickel(II)nitrilotriacetic acid (Qiagen, Chatsworth, Calif.). Purified protein yields of A-Cys, $C_{10}$-Trp, and $AC_{10}$A-Cys were 122 mg, 26 mg, and 56 mg per liter of growth medium, respectively.

Additional Purification and Verification of Protein Synthesis

Figure 20A:
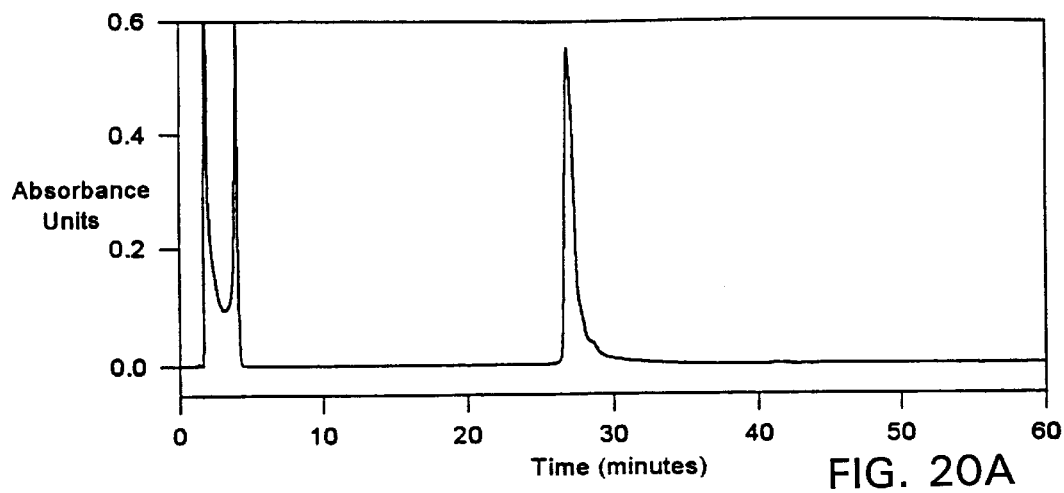
FIGS. 20A, 20B, and 20C are reverse-phase high performance liquid chromatograms of genetically engineered proteins.
Figure 20B:
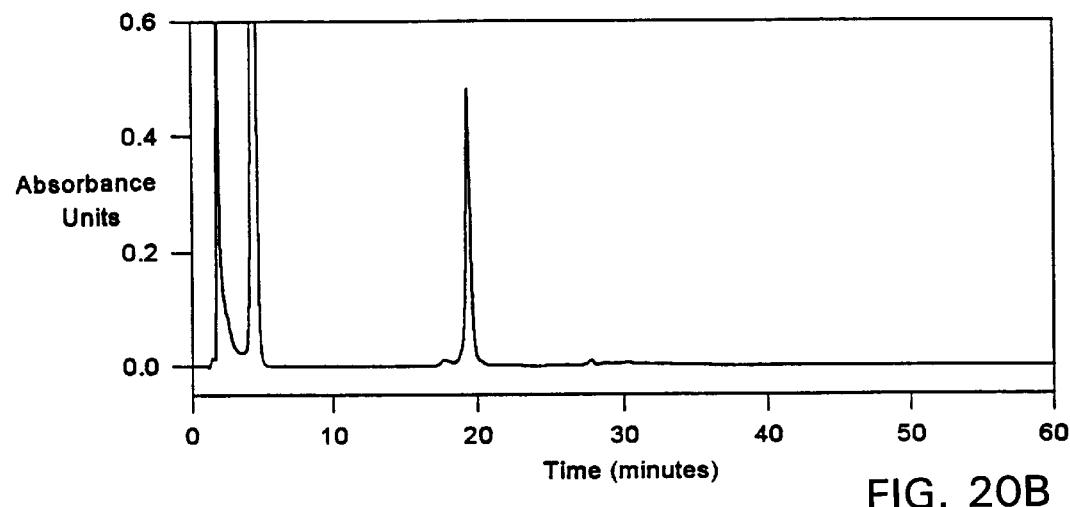
Figure 20C:
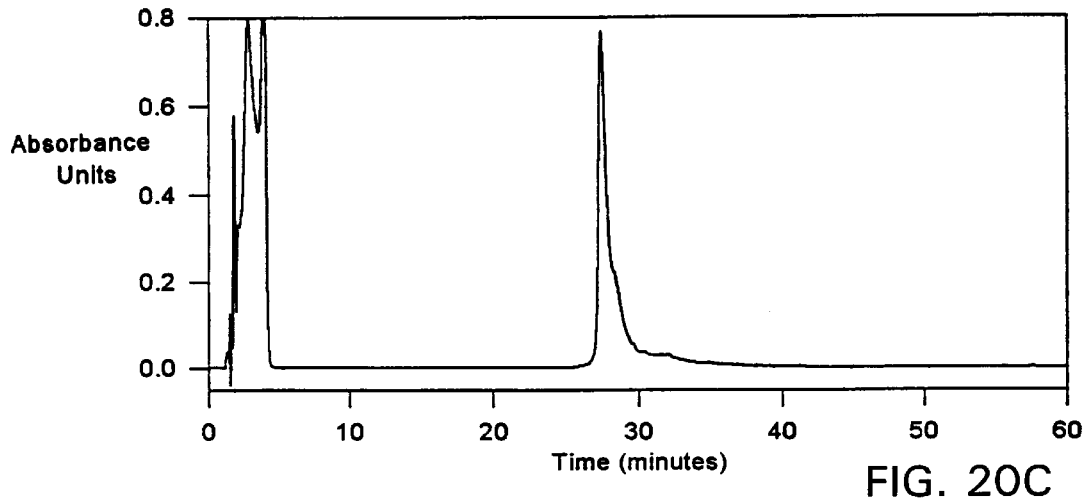

Reverse-phase high performance liquid chromatographs (RP-HPLCs) were acquired on a Waters system (including a Model 717-plus autosampler, a Model 486 tunable absorbance detector, and a Model 600 controller) that was equipped with a VYDAC™ C18 column (Supelco, Bellefonte, Pa.). Proteins were dissolved in distilled, deionized water and filtered (0.22 μm) prior to injection. Elution profiles were monitored at 215 nm with a linear 2% gradient of water (0.1% trifluoroacetic acid) to acetonitrile that was run over a period of 60 minutes at a flow rate of 1 ml/minute. FIGS. 20A, 20B, and 20C are reverse-phase high performance liquid chromatograms of genetically engineered proteins corresponding, respectively, to A-Cys (76 μg) eluted at 26.76 minutes, $C_{10}$-Trp (54 μg) eluted at 19.36 minutes, and $AC_{10}$A-Cys (54 μg) eluted at 27.33 minutes. Solvents were purged with helium. Amino acid compositional analysis, as well as matrix-assisted laser-desorption mass spectrometry (MALDI-MS), were carried out in the Analytical Chemistry and Peptide/DNA Synthesis Facility at Cornell University.

Amino acid compositional analysis was made on a Pico-Tag Amino Acid Analysis System (Millipore Corp., Bedford, Mass.). Amino acids were derivatized with phenyl isothiocyanate (PITC) and analyzed by reverse-phase HPLC with a 4.6×300 mm Nova Pack C18 column (Waters Corp., Bedford, Mass.). All amino acid analyses were within 5% of the theoretical values.

For MALDI experiments, protein samples were mixed with a molar excess of matrix solution (0.05 M 3,5-dimethoxy-4-hydroxycinnamic acid for predicted masses greater than 20,000 and 0.05 M α-cyano-4-hydroxycinnamic acid for predicted masses less than 20,000 in 30% acetonitrile/water, 0.1% trifluoroacetic acid). The probe surface was irradiated with a nitrogen laser at 337 nm. Protein ions were recorded in the positive ion mode at a laser power ranging from 10 to 25 kV. The calculated mass of A-Cys is 8549; a peak was found at 8548. Likewise, the calculated mass of $C_{10}$-Trp is 10383 and a peak was reported at 10433. The calculated mass of $AC_{10}$A-Cys is 22439; the mass analysis gave a peak at 22478, probably due to association of potassium counterion (molecular weight, 39).

Gelation through physical crosslinking requires association of the coiled-coil elements of the block copolymers. To determine whether the unfolding behavior of the helical blocks is affected by attachment of the coil domain, the pH dependence of the transition temperature, $T_m$, was measured for both A-Cys (5 μm) and $AC_{10}$A-Cys (5 μm) in solution. The similarity of the unfolding processes is shown in Table 5. Wavelength scans of $AC_{10}$A-Cys showed a substantial helical contribution to the secondary structure, indicated by minima at 208 nm and 222 nm, which are characteristic wavelengths for the α-helical conformation.

TABLE 5

| Protein | pH | $T_m$ (° C.) |
|---|---|---|
| A-Cys | 6.1 | 88 |
| A-Cys | 6.9 | 64 |
| A-Cys | 7.6 | 51 |
| A-Cys | 9.4 | 50 |
| A-Cys | 10.7 | 40 |
| A-Cys | 11.5 | 31 |
| $AC_{10}$A-Cys | 6.1 | 81 |
| $AC_{10}$A-Cys | 6.9 | 55 |
| $AC_{10}$A-Cys | 7.6 | 54 |
| $AC_{10}$A-Cys | 9.5 | 49 |
| $AC_{10}$A-Cys | 10.8 | 31 |

At pH values greater than 10, the unfolding transitions of both A-Cys and $AC_{10}$A-Cys occur between 30 and 40° C. The low $T_m$ is expected in basic solution, in which the glutamic acid residues are deprotonated and charge—charge repulsion of the helices will occur. In addition, the helical content at 0° C. is reduced from 22055 (pH 7.6) to 16835 (pH 11.5) deg $cm^2$ $dmol^{-1}$ for A-Cys and from 13722 (pH 7.6) to 10294 (10.8) deg $cm^2$ $dmol^{-1}$ for $AC_{10}$A-Cys. This result suggests that the individual helices are partially unfolded at highly basic conditions and low temperatures.

When the pH is lowered to values between 7 and 10, the $T_m$ values increase slightly but are within 10° C. of each other. In the range of pH 7–10 and lower, the lysine (pKa=10) is charged and can form interhelical salt bridges with the glutamic acid. Upon further decrease of the pH to 6, the $T_m$ for A-Cys and $AC_{10}$A-Cys occurs at 88° C. and 81° C., respectively. At pH 5 and lower, no transitions are observed for either protein at temperatures below 100° C. and the helical content decreases only slightly throughout the 0–100° C. temperature range. Acidic conditions effectively stabilize the helix so that no thermal denaturation of A-cys or $AC_{10}$A-cys is observed.

The thermal denaturation experiments described above were carried out in solutions containing 150 mM sodium chloride. Although the addition of sodium chloride (>100 mM) had no significant effect on coiled-coil stability at neutral pH, the stability of the coiled-coil increased drastically in acidic environments. Similar behavior was observed for the helical domains in this study. A thermal melting temperature, $T_m$, was observed for protein A-Cys at 85° C. in 10 mM dibasic sodium phosphate, pH 2.1 (without sodium chloride). No thermal transitions at 222 nm are observed from 0 to 100° C. for either A-Cys or $AC_{10}$A-Cys at pH 2.1. The lack of a thermal transition below 100° C. suggested that the helices were stabilized by the addition of sodium chloride in acidic environments.

Figure 21:
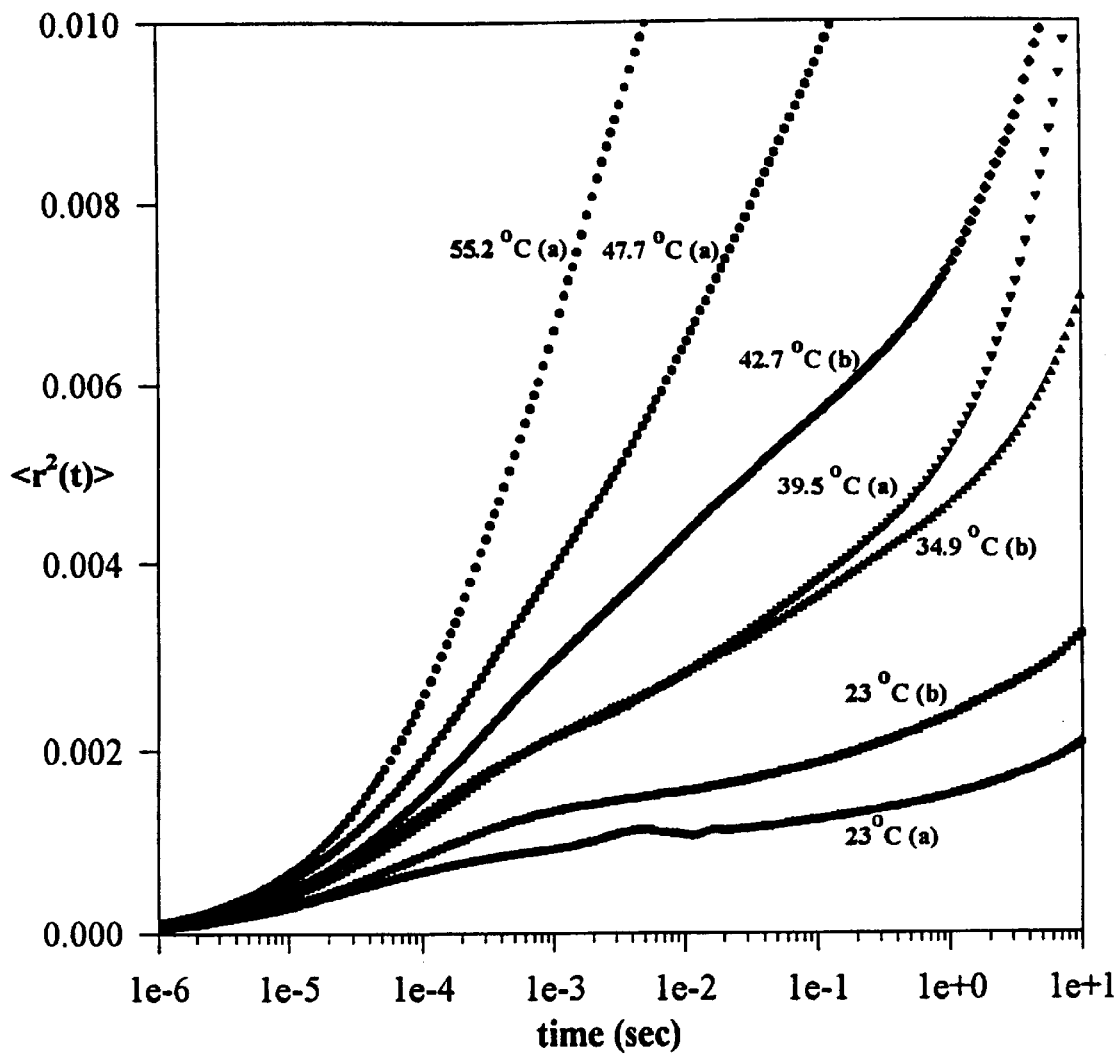
FIG. 21 is a graph of mean square displacement ($r^2$) as a function of time at 23° C. to 55° C. for protein L2AC$_{10}$A.

The thermal dependence of gelation for $AC_{10}$A-Cys was recorded by cycling a 5% gel through a series of temperatures ranging from 23° C. to 55° C. at pH 7.8. The average mean square displacement plotted against time at various temperatures is shown in the graph in FIG. 21. These data were acquired in the following temperature order: 23, 39.6, 47.7, 55.2, 42.7, 24.9, and 23° C. (5% w/v, 10 mM Tris buffer, pH 7.8). In FIG. 21, data collected upon heating the sample from 23° C. to 55.2° C. is represented by (a) and the data collected on cooling the sample from 55.2° C. back down to 23° C. is represented by (b).

Figure 22:
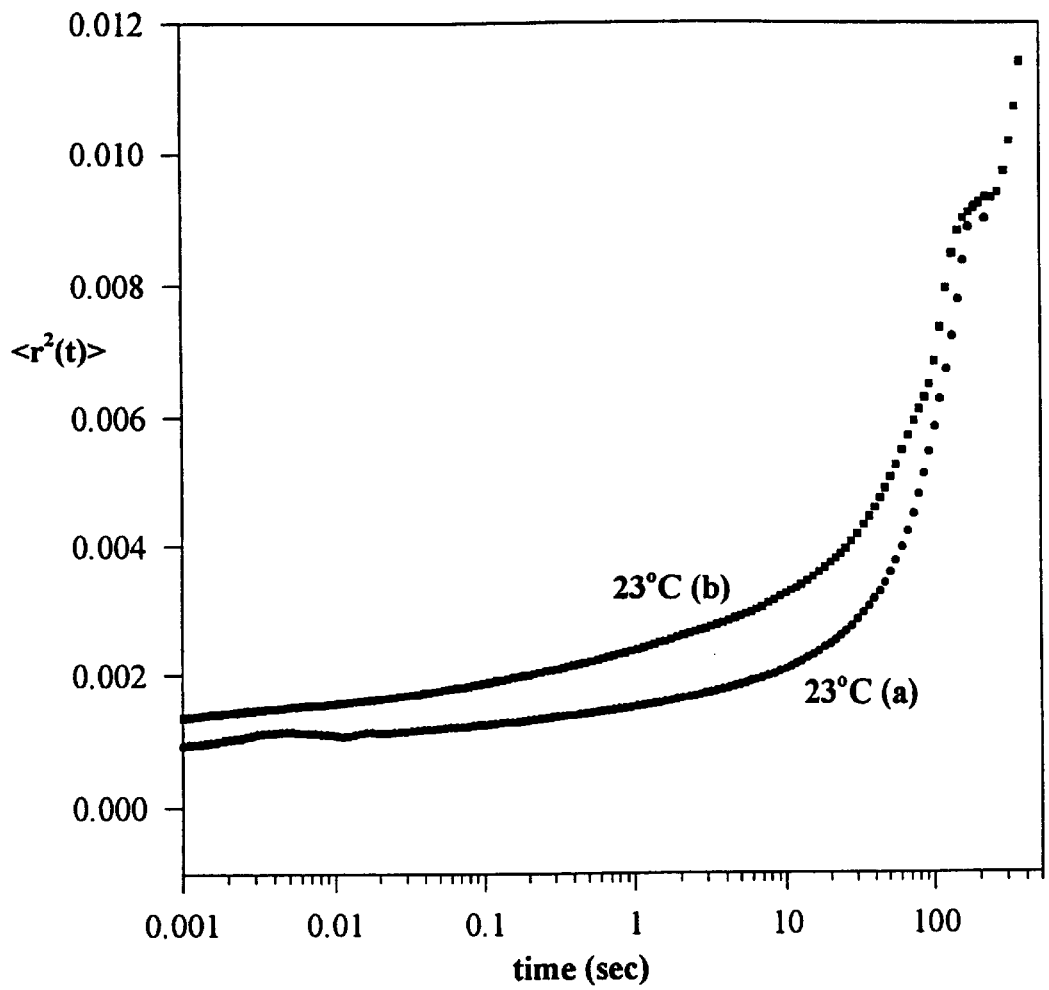
FIG. 22 is a graph of mean square displacement ($r^2$) as a function of time for protein L2AC$_{10}$A at 23° C. (a) before and (b) after thermal cycling.

These data show that as the temperature was increased to 55° C., the gel became more fluid. Interestingly, hysteresis was observed after the material was heated to 55° C. and returned to 23° C. (see FIG. 22, which shows the mean square displacement before, a, and after, b, thermal cycling). This indicates either that equilibrium was not reached or that the gel did not recover 100%.

Figure 23:
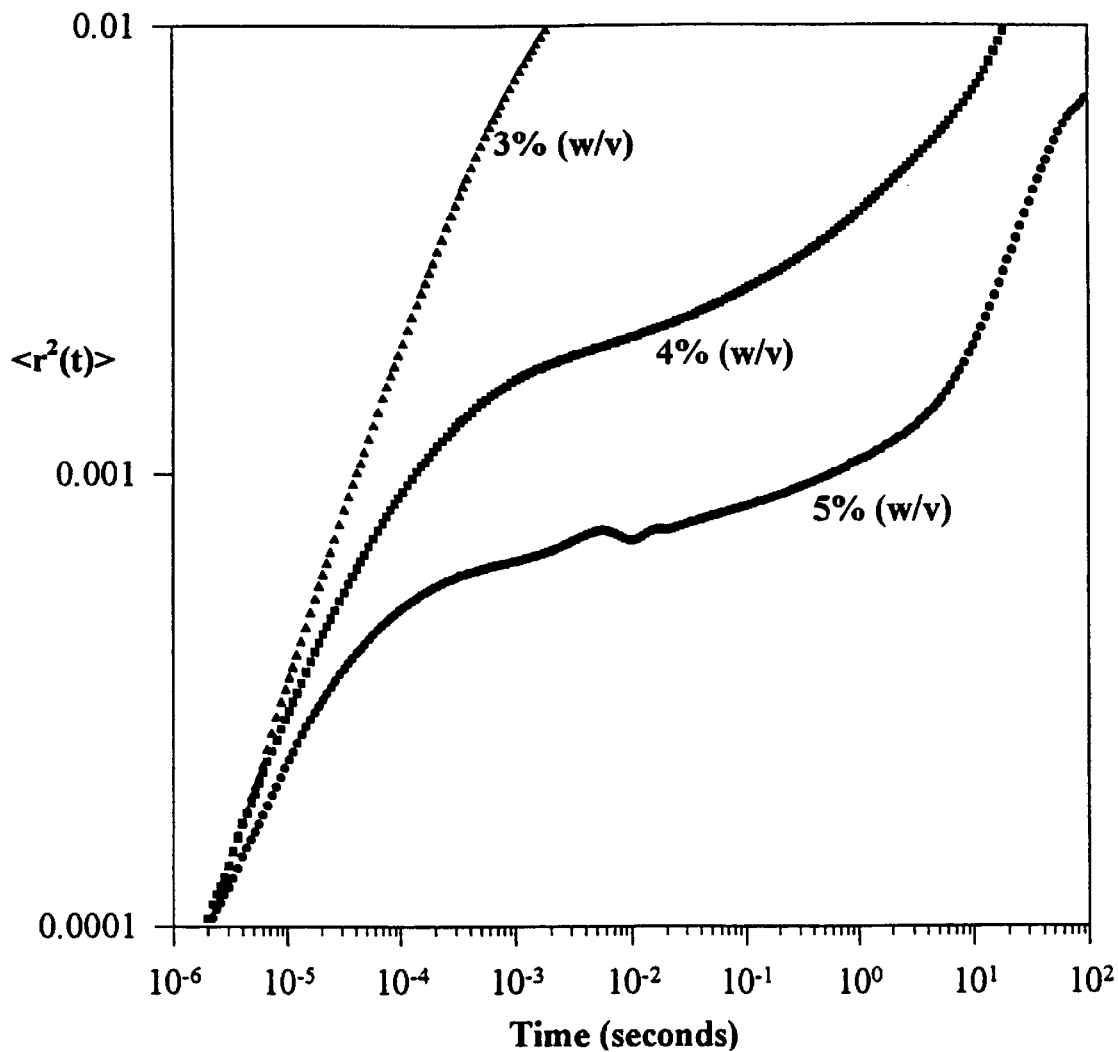
FIG. 23 is a graph of the concentration dependence of the mean square displacement as a function of time for protein L2AC$_{10}$A at varying concentrations.
Figure 24A:
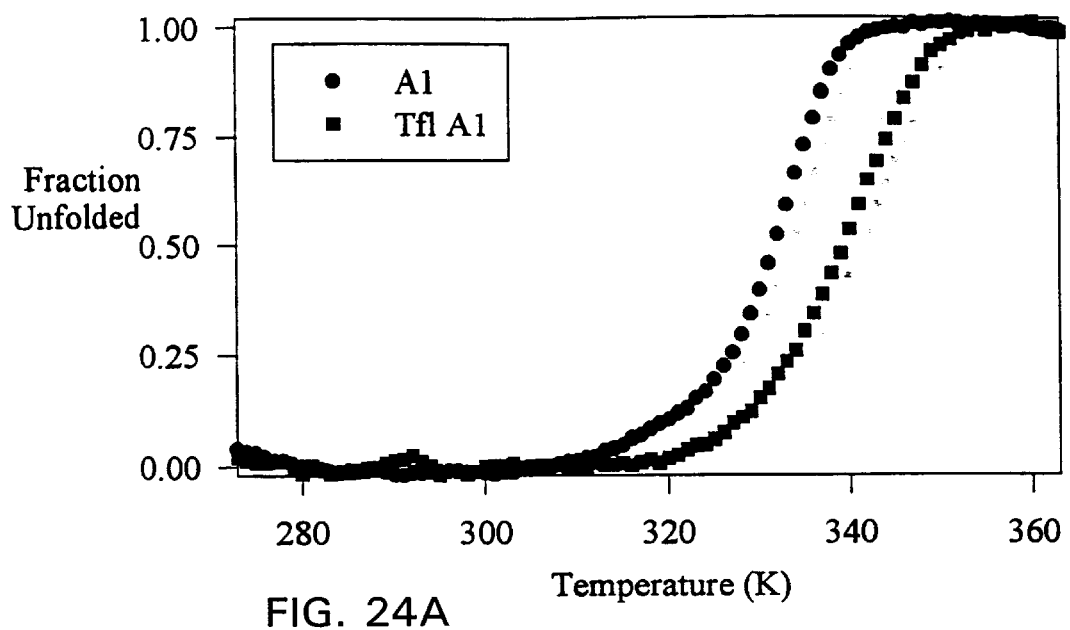
FIGS. 24A and 24B are graphs of the thermal melting profiles of A1 and B1, respectively, with Leu (●) and with Tfl (■).
Figure 24B:
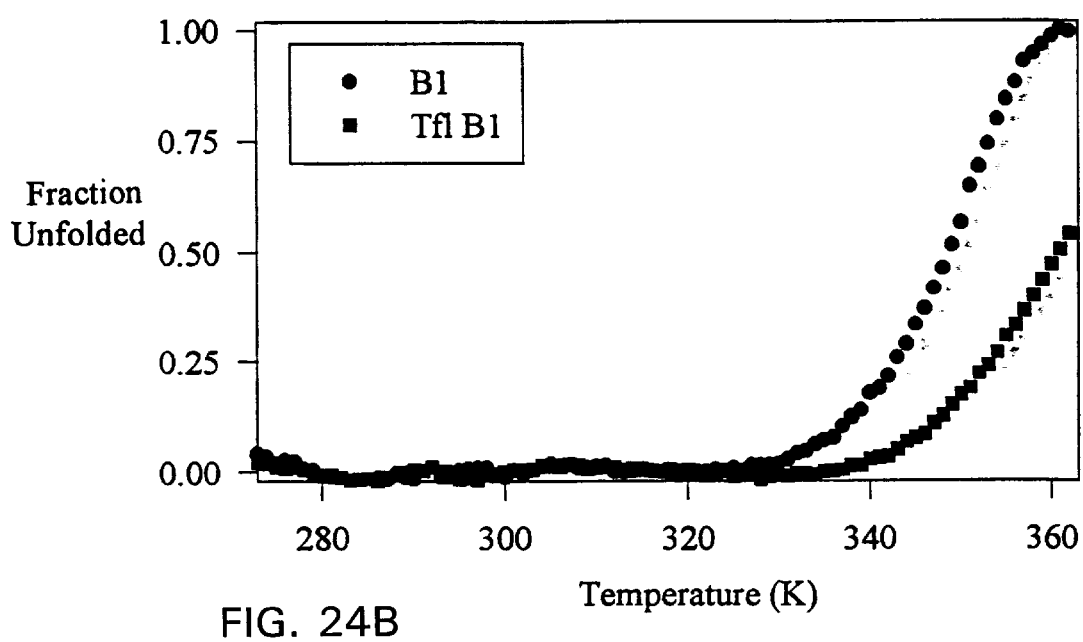

The dependence of gel formation on concentration was also investigated for $AC_{10}$A-Cys at pH 7.9 by diffusing wave spectroscopy (DWS). The DWS spectrum revealed that $AC_{10}$A-Cys became a fluid at 3% (w/v), but $AC_{10}$A-Cys was an elastic medium at 5% (FIG. 23). The 4% sample formed a viscous liquid, at the time of preparation, but the emergence of a plateau was apparent at intermediate times. Therefore, the critical concentration for forming an elastic gel spanning the entire volume of interest was 4–5%. At concentrations of 3–4%, the protein was most likely forming soluble aggregates that viscosified the solution by increasing the apparent molecular weight.

Example 3

Incorporation of 5',5',5'-Trifluoro-L-leucine at the Hydrophobic Interface of Leucine Zippers Leucine auxotrophs of strain MC1000 (F-lacΔx74anaD139/(Ana Abioc-leu)Δ7679 gal U gal K rspL) containing pREP4 plasmid (Qiagen, Chatsworth, Calif.) were used. The stable auxotroph was designated JM-1. Expression vectors containing A1 and B1 DNA sequences (pQE9-A1 and pQE9-B1) were used.

General Methods

Electrospray mass spectra were collected on a FISONS VG PLATFORM II™ electrospray mass spectrometer. A1 and B1 protein spectra were recorded as standards. All samples were run in 50:50 acetonitrile:water with 0.2% formic acid at 12 pmol/μl concentrations. Data were recorded in a positive ion mode (full scan 600–1500 m/z), with an infusion rate of 5 μl/minute and cone voltages of 35 and 50 V.

A Waters high performance liquid chromatography (HPLC) system (including a Model 717-plus autosampler, a Model 486 tunable absorbance detector, and a Model 600 controller) was used to inject 50 μl samples at flow rates of 1 ml/min onto a VYDAC™ C18 (Supelco, Bellefonte, Pa.) reversed phase column. MILLENNIUM™ (Waters Corp., Milford, Mass.) software was used in the analysis of the collected spectra at 210 nm. The samples were eluted over 60 minutes with a gradient of water/0.1% trifluoroacetic acid (TFA) and acetonitrile/0.1% TFA. The gradient included 90:10 (10 min), 50:50 (20 min), and 100:0 (30 min) ratios. Amino acid analysis was carried out on a PICO-TAG™ Amino Acid Analysis System. Duplicate samples were hydrolyzed in constant boiling hydrochloric acid at 150° C. for 110 minutes. Appropriate blanks, controls and standards were hydrolyzed in the same vessel as a batch hydrolysis. The amino acids were derivatized with phenylisothiocyanate (PITC) and analyzed by reverse-phase HPLC. The resulting phenylthiocarbamoyl amino acid derivatives were separated on a 4.6×300 mm Nova Pack C18 column, using a modified Pico-Tag buffer system. Circular dichroism spectra were recorded on an Aviv 62DS spectropolarimeter (Lakewood, N.J.). Mean residue molar ellipticity reported at 222 nm ($[\theta]_{222}$, deg cm² dmol⁻¹) was calculated from the following equation:

$$[\theta]=[\theta]_{obs} \times MRW/(c \times 1)$$

where $[\theta]_{obs}$ is ellipticity measured in millidegrees, MRW is the mean residue molecular weight (i.e., molecular weight of the peptide divided by the number of amino acid residues), c is the peptide concentration in g/l determined by quantitative amino acid analysis, and 1 is the optical path length in mm. Thermal melting curves were determined by monitoring the CD signal of the protein solutions (3 μM) at 222 nm as a function of temperature. Data was collected from 0 to 90° C. in 1° C. increments with an equilibration time of 1 minute. Spectra were collected in 50 mM sodium phosphate buffer, 100 mM sodium chloride, pH 7.4. Two Peltier units on both sides of the 1 cm path length rectangular cell (Helma) were used to regulate the temperature to within ±0.2° C.

Thermal melting temperature, $T_m$, was calculated as the temperature at which 50% of the helix is unfolded, using a two-state mechanism to describe the equilibrium between folded and unfolded protein states. To get this value, ellipticity readings were normalized to the fraction of the protein folded using the standard equation:

$$f_n=([\theta]-[\theta]_u)/([\theta]_n-[\theta]_u)$$

where $[\theta]_n$ and $[\theta]_u$ represent the ellipticity values for the fully folded and fully unfolded species, respectively, at 222 nm. All thermal melting transitions were determined to be reversible (±2° C.) with 96%, 88%, 99%, and 97% of the initial helix contents of A1, B1, Tfl A1, and Tfl B1, respectively.

Protein Expression and Purification pQE9-A1 and pQE9-B1 were used to transform strain mc1000 (F-lacΔx74anaD139/(Ana Abioc-leu)Δ7679 gal U gal K rspL) containing pREP4 to yield JM-1/pQE9-A1 and JM-1/pQE9-B1. Single colonies of cells were grown to saturation in 5 ml of 2xYT medium (16 g Bacto-Tryptone, 10 g yeast extract, 5 g sodium chloride per liter) containing ampicillin (200 μg/ml) and kanamycin (25 μg/ml) overnight at 37° C. Each of these cultures was transferred to 1 l of sterilized YT medium containing the same concentrations of antibiotics. The cells were incubated until optical densities at 600 nm ($OD_{600}$) reached 1 and then centrifuged at 5000 rpm for 10 minutes. The supernatant was then decanted and the cells were washed with 1 l of 1% M9 salt solution (containing 60 g dibasic sodium phosphate, 30 g monobasic potassium phosphate, 5 g sodium chloride, and 10 g ammonium chloride per liter). Again the cells were pelleted and resuspended in 2 l of M9 medium (containing 10% v/v M9 salt solution, 10% 19 amino acid solution (0.4 g of each amino acid, except leucine, per liter), 0.1% 1 M magnesium sulfate heptahydrate, 0.1% 0.01 M calcium chloride, 0.1% vitamin $B_1$, 4% glucose (20% w/v solution), 0.33% ampicillin (200 μg/ml), 0.16% kanamycin (25 μg/ml) and 75.3% distilled deionized water). Leucine (40 mg/ml; final concentration of 40 μg/ml) or 5',5',5'-trifluoro-D,L-leucine (40 mg/ml; final concentration of 40 μg/ml; MTM Research Chemicals, Windham, N.H.) was added in addition to the M9 medium. The cells were grown for 15 minutes, then isopropyl-β-thiogalactoside (IPTG, 1 mM) was added to induce protein synthesis. Cell cultures were removed and centrifuged at 5000 rpm for 10 minutes at various times after induction with IPTG. All pelleted cells were resuspended in 25 ml of lysis buffer (6 M guanidine-HCl, 0.1 M dibasic sodium phosphate, pH 8) and placed in −80° C. freezer overnight. The supernatants from the cell lysates were subjected to nickel(II)-NTA metal affinity chromatography. The collected protein fractions were frozen at −80° C. and lyophilized to give total dry weights for all proteins of 75–100 mg per liter of growth medium.

The in vivo synthesis of Tfl A1 and Tfl B1 was followed after the culture was shifted to minimal medium supplemented with amino acids. Protein accumulation was monitored for three hours after induction with IPTG (1 mM) and was visualized on a 15% SDS-polyacrylamide gel with Coomassie Brilliant Blue R-250. Prior to induction there was no protein accumulation; one to three hours after induction, cells in medium containing either Leu or Tfl showed protein expression. Substitution of Tfl for leucine in A1 and B1 was confirmed by electrospray mass spectrometry.

Initial measurements of the thermal stabilities of α-helical Leu and Tfl containing A1 and B1 were made by circular dichroism spectroscopy (Table 6 and FIGS. 24A and 24B). Table 6 lists the thermal melting transitions of A1, Tfl A1, B1, and Tfl B1, monitored at 222 nm; $T_m$ is the temperature at which 50% of the helix is unfolded in 50 mM sodium phosphate, 100 mM sodium chloride, pH 7.4.

The thermal stabilities of the Tfl-substituted helices recorded at 222 nm showed that 66% replacement of leucine with trifluoroleucine in A1 only resulted in an 8° C. increase in $T_m$, whereas 38% replacement in B1 resulted in a 13° C. increase in $T_m$ (the spectra were acquired in 50 mM dibasic sodium phosphate and 100 mM sodium chloride, pH 7.4,

| Dimer Complex | $T_m$ in PBS (° C.)[a] |
|---|---|
| A1—A1 | 58 |
| Tfl A1—Tfl A1 | 66 |
| B1—B1 | 75 |
| Tfl B1—Tfl B1 | 88 | at protein concentrations of 3 μM). These data suggested that the increased level of Tfl destabilized the helix—helix interactions due to: (1) the increased size of fluorine over that of hydrogen, (2) the difference in chemical character between fluorine and hydrogen, or (3) both the differences in size and character. The introduction of Tfl at the d position in the heptad repeat can disrupt the overall packing of coiled-coils.

At lower levels of Tfl substitution, the effect of increased size and electronegativity on the packing density can be less significant than at higher levels. The interaction between fluorine and hydrogen is relatively unfavorable; thus, at intermediate levels of Tfl substitution, the helices are destablized. At near complete Tfl substitution at the d position, however, it is thought the helices would be very stable due to favorable fluorine—fluorine interaction.

In general, the results demonstrate that coiled-coils became more thermally stable with relatively low levels of Tfl substitution. The use of leucine auxotrophs to prepare unique coiled-coil proteins containing Tfl groups can be applied to a variety of proteins where Leu participates in folding, stability, activity, or function. With optimization of this strategy, the enhancement of certain physical properties in natural polymer systems can be achieved for biological or materials applications.

Example 4

Use of a Hydrogel as a Wound Dressing

A solution is made from the $AC_{10}A$ copolymer. This solution forms a stable gel at around pH 7 over a broad range of temperatures (i.e., including at least 25 to 37° C.) as a result of the interaction and packing of the coiled-coil structure. The pH of the gelled solution is increased to 12, at which the solution liquifies. A topical antibiotic drug (e.g., neosporin) is dissolved in the solution and loaded into an aerosol can for later use.

A brief burst of the aerosol is used to dress a wound on a patient (e.g., an abrasion, burn, or non-puncture wound). When the aerosol contacts the patient's skin, the pH of the solution is partly neutralized by water, sweat, or blood on the skin's surface, thereby causing the copolymer to form a protective medicated gel covering the wound.

Example 5

Use of a Copolymer to Promote Healing

A copolymer is produced from a gene that encodes a derivative of $AC_{10}A$ with a cell binding domain inserted in the middle of the random coil block. The cell binding domain is the integrin ArgGlyAspSer SEQ ID NO: 22 sequence, which is known to bind to gpIIa/IIIa proteins expressed on fibroblast cells necessary for matrix formation for the regeneration of skin. The $AC_{10}A$ protein is chosen because it is a gel under physiological conditions (i.e., pH 7.4, 37° C.). The produced copolymer is suspended in water to form a gel, which is then is used to treat a wound. Fibroblasts become entrapped within the gel and thus remain at the site of the wound, serving as a scaffold for the regeneration of tissue surrounding the wound.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A synthetic block copolymer XYZ, comprising:
two α-helical protein blocks X and Z, each having an amino acid sequence and conformation that allow each α-helical protein block to form a coiled-coil with an α-helical protein block on another block copolymer XYZ;
a water-soluble, random-coil protein block Y, the random-coil protein block linking the two α-helical protein blocks; and
linker proteins that link the α-helical protein blocks to the random-coil protein block.

2. A synthetic block copolymer comprising:
at least two α-helical protein blocks, each having an amino acid sequence and conformation that allow each α-helical protein block to form a coiled-coil with an α-helical protein block on another molecule of the block copolymer, wherein each α-helical protein block comprises at least 28 amino acids; and at least one water-soluble, random-coil protein block comprising at least 15 amino acids, the random-coil protein block linking at least two of the α-helical protein blocks.

3. A synthetic block copolymer XYZ, comprising:

two α-helical protein blocks X and Z, each having an amino acid sequence and conformation that allow each α-helical protein block to form a coiled-coil with an α-helical protein block on another block copolymer XYZ, wherein each α-helical protein block comprises at least 28 amino acids; and a water-soluble, random-coil protein block Y comprising at least 15 amino acids, the random-coil protein block linking the two α-helical protein blocks.

4. A block copolymer of claim 3, wherein X and Z are identical to each other.

5. A block copolymer of claim 3, wherein X and Z are non-identical.

6. A block copolymer of claim 3, wherein Y has the sequence [(AlaGly)$_p$ProGluGly]$_n$(SEQ ID NO: 23), where p is 0 to 4 and n is 5 to 100.

7. A block copolymer of claim 6, wherein n is 8 to 54.

8. A block copolymer of claim 6, wherein p is 3.

9. A block copolymer of claim 3, wherein the sequences of amino acids that make up X and Z have an (ABCDEFG)$_m$ (SEQ ID NO: 24) pattern; wherein m is 4 to 100; A and D are hydrophobic amino acids; E and G are polar amino acids; and B, C, and F can be any amino acid.

10. A block copolymer of claim 9, wherein m is 6 to 18.

11. A block copolymer of claim 9, wherein more than 80% of the E and G amino acids of X are acidic amino acids and more than 80% of the E and G amino acids of Z are basic amino acids.

12. A block copolymer of claim 9, wherein more than 80% of the E amino acids of X and G amino acids of Z are acidic amino acids and more than 80% of the E amino acids of Z and G amino acids of X are basic amino acids.

13. A block copolymer of claim 9, wherein more than 80% of the E amino acids of X and Z are acidic amino acids and more than 80% of the G amino acids of X and Z are basic amino acids.

14. A synthetic block copolymer comprising:

at least two α-helical protein blocks, each having an amino acid sequence and conformation that allow each α-helical protein block to form a coiled-coil with an α-helical protein block on another molecule of the block copolymer; and at least one water-soluble, random-coil protein block, the random-coil protein block linking at least two of the α-helical protein blocks, wherein the water-soluble, random-coil protein block has the sequence [(AlaGly)$_p$ProGluGly]$_n$(SEQ ID NO: 23), where p is 0 to 4 and n is 5 to 100.

15. A block copolymer of claim 14, wherein n is 8 to 54.

16. A block copolymer of claim 14, wherein p is 3.

17. A synthetic block copolymer comprising:

at least two α-helical protein blocks, each having an amino acid sequence and conformation that allow each α-helical protein block to form a coiled-coil with an α-helical protein block on another molecule of the block copolymer, wherein the sequence of amino acids that make up at least one of the α-helical protein blocks has an (ABCDEFG)$_m$(SEQ ID NO: 24), pattern; wherein m is 4 to 100; A and D are hydrophobic amino acids; E and G are polar amino acids; and B, C, and F can be any amino acids; and at least one water-soluble, random-coil protein block, the random-coil protein block linking at least two of the α-helical protein blocks.

18. A block copolymer of claim 17, wherein m is 6 to 18.

19. A synthetic block copolymer XYZ comprising:

two α-helical protein blocks X and Z, each having an amino acid sequence and conformation that allow each α-helical protein block to form a coiled-coil with an α-helical protein block on another block copolymer XYZ;

a water-soluble, random-coil protein block Y, the random-coil protein block linking the two α-helical protein blocks; and a recognition sequence or other peptidic target sequence that specifically binds to a macromolecule.

20. A synthetic block copolymer XYZ comprising:

two α-helical protein blocks X and Z, each having an amino acid sequence and conformation that allow each α-helical protein block to form a coiled-coil with an α-helical protein block on another block copolymer XYZ;

a water-soluble, random-coil protein block Y, the random-coil protein block linking the two α-helical protein blocks; and a recognition sequence or other peptidic target sequence that specifically binds to a cell.

21. A block copolymer of claim 20, wherein the cell is a fibroblast.

22. A block copolymer of claim 20, wherein the recognition sequence comprises the sequence ArgGlyAsp.

23. A gel, comprising:

a liquid and a block copolymer of claim 3 suspended in the liquid to form a suspension.

24. A gel of claim 23, wherein the liquid is an aqueous liquid.

25. A gel of claim 24, wherein the aqueous liquid is water.

26. A gel of claim 23, wherein the suspension is monodisperse.

27. A gel comprising:

a liquid and the block copolymer of claim 19 suspended in the liquid.

28. A gel, comprising:

a liquid and a block copolymer of claim 2 suspended in the liquid.

29. A wound dressing comprising a synthetic block copolymer XYZ and an antibiotic compound, wherein the copolymer and the antibiotic are both dissolved in a liquid, and the copolymer comprises:

two α-helical protein blocks X and Z, each having an amino acid sequence and conformation that allow each α-helical protein block to form a coiled-coil with an α-helical protein block on another block copolymer XYZ; and a water-soluble, random-coil protein block Y, the random-coil protein block linking the two α-helical protein blocks.

30. A method of dressing an abrasion, burn or non-puncture wound comprising applying the block copolymer of claim 3 to said wound.

* * * * *

UNITED STATES PATENT AND TRADEMARK OFFICE
CERTIFICATE OF CORRECTION

PATENT NO.    : 6,090,911
DATED         : July 18, 2000
INVENTOR(S)   : Petka et al.

It is certified that error appears in the above-identified patent and that said Letters Patent is hereby corrected as shown below:

<u>Title page,</u>
Item [73], please add -- and Government of the United States/Department of the Army --

<u>Column 1,</u>
Line 2, please insert before the BACKGROUND OF THE INVENTION -- The invention was made with Government support under a contract awarded by the U.S. Army Soldier Systems Center, Natick, MA 01760. The Government has certain rights in the invention. --

Signed and Sealed this

Second Day of September, 2003

JAMES E. ROGAN
*Director of the United States Patent and Trademark Office*